US 6,468,762 B1
United States Patent
Tan
Date of Patent: *Oct. 22, 2002

(54) HIGH SPECIFICITY HOMOCYSTEINASES

(75) Inventor: Yuying Tan, San Diego, CA (US)

(73) Assignee: AntiCancer, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/549,098

(22) Filed: Apr. 12, 2000

Related U.S. Application Data

(63) Continuation-in-part of application No. 09/340,991, filed on Jun. 28, 1999, now Pat. No. 6,066,467, which is a continuation-in-part of application No. 09/122,129, filed on Jul. 24, 1998, now Pat. No. 5,998,191, which is a continuation-in-part of application No. 09/061,337, filed on Apr. 17, 1998, now Pat. No. 5,985,540, which is a continuation-in-part of application No. 08/974,609, filed on Nov. 19, 1997, now Pat. No. 6,140,102, which is a continuation-in-part of application No. 08/941,921, filed on Oct. 1, 1997, now abandoned, which is a continuation-in-part of application No. 08/918,214, filed on Aug. 25, 1997, now abandoned, which is a continuation-in-part of application No. 08/899,776, filed on Jul. 24, 1997, now abandoned.

(51) Int. Cl.$^7$ .............................. C12Q 1/37; C12Q 1/00
(52) U.S. Cl. ............................... 435/24; 435/4; 435/23; 536/23.1; 536/23.2
(58) Field of Search ................................ 435/24, 4, 23; 536/23.1, 23.2

(56) References Cited

U.S. PATENT DOCUMENTS

| 4,681,841 A | 7/1987 | Matsumoto et al. ........... 435/24 |
| 4,940,658 A | 7/1990 | Allen et al. ...................... 435/24 |
| 5,094,947 A | 3/1992 | Nakajima et al. .............. 435/24 |
| 5,438,017 A | 8/1995 | Allen et al. ...................... 435/24 |
| 5,478,729 A | 12/1995 | Van Atta et al. ................ 435/24 |
| 5,631,127 A | 5/1997 | Sundrehagen ................. 435/24 |
| 5,827,645 A | 10/1998 | Sundrehagen et al. ......... 435/24 |
| 5,985,540 A | * 11/1999 | Tan et al. ........................ 435/4 |
| 5,998,191 A | * 12/1999 | Tan et al. ........................ 435/4 |
| 6,066,467 A | * 5/2000 | Xu et al. ......................... 435/23 |
| 6,140,102 A | * 10/2000 | Tan et al. ........................ 435/4 |

FOREIGN PATENT DOCUMENTS

| WO | WO 93/15220 | 8/1993 |
| WO | WO 98/07872 | 2/1998 |
| WO | WO 98/14562 | 4/1998 |
| WO | WO 99/05311 | 2/1999 |

OTHER PUBLICATIONS

Araki, A. et al., *Journal of Chromatography* (1987) 422 : 43–52.

Bagnara, A.S. et al., *Molecular and Biochemical Parasitology* (1996) 81 : 1–11.

Dudman, N.P.B. et al., *Clinical Chemistry* (1996) 42 (12) : 2028–2032.

Esaki, N. et al., "L–Methionine gamma–Lyase from *Pseudomonas putida* and *Aeromonas*" in *Methods in Enzymology* (1987) 143 : 459–465.

Gage, D.A. et al., *Nature* (1997) 387 : 891–893.

Garg, U.C., *Clinical Chemistry* (1997) 43(1) : 141–145.

Gilfix, B.M. et al., *Clinical Chemistry* (1997) 43(4) : 687–688.

(List continued on next page.)

Primary Examiner—Louise N. Leary
(74) Attorney, Agent, or Firm—Morrison & Foerster LLP

(57) ABSTRACT

Homocysteinase enzymes are disclosed which have sufficient specificity for homocysteine, as compared to cysteine that hydrogen sulfide can be used as a measure of homocysteine in a biological fluid even in the presence of substantial amounts of cysteine, exceeding the level of homocysteine. The enzyme of desired specificity can be readily prepared by mutation and screening of naturally occurring homocysteinases or by constructing chimeric forms.

18 Claims, 7 Drawing Sheets

OTHER PUBLICATIONS

Han, Q. et al. *Protein Expression and Purification* (1998) 14(2):267–274.

Hoffman, R.M. et al., "Diagnosis and treatment of homocysteine disease using recombinant homocysteinase". 2nd International Conference on Homocysteine Metabolism Nijmegen, Netherlands, Apr. 26–29, 1998. Netherlands Journal Of Medicine 52 (Suppl) 1998. S41. ISSN: 0300–2977, XP002087823.

Hori, H. et al., *Cancer Research* (1996) 56 : 2116–2122.

Inoue, Y. et al., *Applied Microbiology and Biotechnology* (1993) 38 : 473–477.

Ito, S. et al. *Journal of Biochemistry* (1976) 79 : 1263–1272.

Jakubowsky, H. et al., *FEBS Letters* (1993) 317(3) : 237–240.

Kang, S. et al., *Annual Review of Nutrition* (1992) 12 : 279–298.

Kerr, R.A. *Science* (1997) 276 : 703–704.

Lockwood, B. et al., *Biochemical Journal* (1991) 279 : 675–682.

Markos, A. et al., *FEMS Microbiology Letters* (1996) 135 : 259–264.

McCully, K.S., *American Journal of Pathology* (1969) 56 : 111–128.

McCully, K.S., *Annals of Clinical and Laboratory Science* (1993) 23(6) : 477–493.

McCully, K.S., *Annals of Clinical and Laboratory Science* (1994) 24(1) : 27–59.

McCully, K.S., *Annals of Clinical and Laboratory Science* (1994) 24(2) : 134–152.

McCully, K.S., *Nature Medicine* (1996) 2(4) : 386–389.

McKie, A. et al., *Journal of Biological Chemistry* (1998) 273 : 5549–5556.

Mottram, J.C., Gene Bank, (Jul. 17, 1997), Accession No. AJ000486, NID g2330884; and Accession No. AJ000487, NID g2330886.

Mudd, S.H. et al., *American Journal of Human Genetics* (1985) 37 : 1–31.

Nygard, O. et al., *The New England Journal of Medicine* (1997) 337(4) : 230–236.

Pennist, E., *Science* (1997) 276 : 705–706.

Refsum et al. *Clinical Chemistry* (1985) 31/4:624–627.

Riley, D.E. et al., *Molecular and Biochemical Parasitology* (1992) 51 : 161–164.

Robinson, K. et al., *Cleveland ClinicJournal of Medicine,* (1994) 61(6):438–450.

Sambrook et al. In: *Molecular Cloning 3*, 2d edition, Cold Spring Harbor Laboratory Press, (1989) pp. 17.30–17.33.

Selhub, J. et al., *New England Journal. of Medicine* (1995) 332 : 286–291.

Shipchandler, M.T. et al., *Clinical Chemistry* (1995) 41(7) : 991–994.

SIGMA Catalog. Biochemicals Organic Compounds for Research and Diagnostic Reagents (1993), pp. 175, 377, 984.

Stampfer, M. et al, *Journal of the American Medical Association* (1992) 268 : 877–881.

Tan, Y. et al., *Protein Expression and Purification* (1997) 9 : 233–245.

Tanaka, H. et al., *Journal of Applied Biochemistry* (1980) 2 : 439–444.

Tanaka, H. et al., *Biochemistry* (1977) 16 : 100–106.

Thong, K–W. et al., *Experimental Parasitology* (1987) 63 : 143–151.

Thong, K–W. et al., *IRCS Journal of Medical Science* (1985) 13 : 493–494.

Thong, K–W. et al., *IRCS Journal of Medical Science* (1985) 13 : 495–496.

Thong, K–W. et al., *Molecular and Biochemical Parasitology* (1987) 23 : 223–231.

Ueland, P. et al., "Plasma Homocysteine and Cardiovascular Disease", in *Atherosclerotic Cardiovascular Disease, Hemostasis and Endothelial Function*, Francis, R.B. Jr., ed., 1992, pp. 183–236, Marcel Dekker, Inc , New York.

Vilaseca, M.A. et al., *Clinical Chemistry* (1997) 43(4) : 690–691.

Watanabe, K. et al., *Nucleic Acids Research* (1986) 14 : 4393–4400.

Wiebers et al. *J Biol Chem* (1967) 242(1):12–23.

Wolfe, G.V. et al., *Nature* (1997) 387 : 894–897.

Yamaguchi, A. et al., Annual Report of Sapporo City Institute of Public Health (1993) 20 : 67–74.

Zuo, X. et al., *Microbiology* (1995) 141 : 2637–2642.

\* cited by examiner

```
AC2-1                                                  Met His His His His His His
MGL1                                                   --- --- --- --- --- --- ---
                                                       -7          -5
AC2-1  Met Ser His Glu Arg Met Thr Pro Ala Thr Ala Cys Ile His Ala Asn
MGL1   Met Ser His Glu Arg Met Thr Pro Ala Thr Ala Cys Ile His Ala Asn
       1               5               10                      15
AC2-1  Pro Gln Lys Asp Gln Phe Gly Ala Ala Ile Pro Pro Ile Tyr Gln Thr
MGL1   Pro Gln Lys Asp Gln Phe Gly Ala Ala Ile Pro Pro Ile Tyr Gln Thr
                   20              25                      30
AC2-1  Ser Thr Phe Val Phe Asp Asn Cys Gln Gln Gly Gly Asn Arg Leu Ala
MGL1   Ser Thr Phe Val Phe Asp Asn Cys Gln Gln Gly Gly Asn Arg Phe Ala
               35              40                      45
AC2-1  Gly Gln Glu Ser Gly Tyr Ile Tyr Thr Arg Leu Gly Asn Pro Thr Val
MGL1   Gly Gln Glu Ser Gly Tyr Ile Tyr Thr Arg Leu Gly Asn Pro Thr Val
           50              55                      60
AC2-1  Ser Asn Leu Glu Gly Lys Ile Ala Phe Leu Glu Lys Thr Glu Ala Cys
MGL1   Ser Asn Leu Glu Gly Lys Ile Ala Phe Leu Glu Lys Thr Glu Ala Cys
       65              70              75                      80
AC2-1  Val Ala Thr Ser Ser Gly Met Gly Ala Ile Ala Ala Thr Val Leu Thr
MGL1   Val Ala Thr Ser Ser Gly Met Gly Ala Ile Ala Ala Thr Val Leu Thr
                       85              90                      95
AC2-1  Ile Leu Lys Ala Gly Asp His Leu Ile Ser Asp Glu Cys Leu Tyr Gly
MGL1   Ile Leu Lys Ala Gly Asp His Leu Ile Ser Asp Glu Cys Leu Tyr Gly
                   100             105                     110
AC2-1  Cys Thr His Ala Leu Phe Glu His Ala Leu Thr Lys Phe Gly Ile Gln
MGL1   Cys Thr His Ala Leu Phe Glu His Ala Leu Thr Lys Phe Gly Ile Gln
               115             120                     125
AC2-1  Val Asp Phe Ile Asn Thr Ala Ile Pro Gly Glu Val Lys Lys His Met
MGL1   Val Asp Phe Ile Asn Thr Ala Ile Pro Gly Glu Val Lys Lys His Met
           130             135                     140
AC2-1  Lys Pro Asn Thr Lys Ile Val Tyr Phe Glu Thr Pro Ala Asn Pro Thr
MGL1   Lys Pro Asn Thr Lys Ile Val Tyr Phe Glu Thr Pro Ala Asn Pro Thr
       145                 150                 155                 160
AC2-1  Leu Lys Ile Ile Asp Met Glu Arg Val Cys Lys Glu Ala His Ser Gln
MGL1   Leu Lys Ile Ile Asp Met Glu Arg Val Cys Lys Asp Ala His Ser Gln
                       165                 170                 175
AC2-1  Glu Gly Val Leu Val Ile Ala Asp Asn Thr Phe Cys Ser Pro Met Ile
MGL1   Glu Gly Val Leu Val Ile Ala Asp Asn Thr Phe Cys Ser Pro Met Ile
                       180                 185                 190
```

*FIG. 1A*

```
AC2-1  Thr Asn Pro Val Asp Phe Gly Val Asp Val Val Val His Ser Ala Thr
MGL1   Thr Asn Pro Val Asp Phe Gly Val Asp Val Val Val His Ser Ala Thr
               195                 200                 205
AC2-1  Lys Tyr Ile Asn Gly His Thr Asp Val Val Ala Gly Leu Ile Cys Gly
MGL1   Lys Tyr Ile Asn Gly His Thr Asp Val Val Ala Gly Leu Ile Cys Gly
               210                 215                 220
AC2-1  Lys Ala Asp Leu Leu Gln Gln Ile Arg Met Val Gly Ile Lys Asp Ile
MGL1   Lys Ala Asp Leu Leu Gln Gln Ile Arg Met Val Gly Ile Lys Asp Ile
               225             230                 235             240
AC2-1  Thr Gly Ser Val Ile Ser Pro His Asp Ala Trp Leu Ile Thr Arg Gly
MGL1   Thr Gly Ser Val Ile Ser Pro His Asp Ala Trp Leu Ile Thr Arg Gly
                       245                 250                 255
AC2-1  Leu Ser Thr Leu Asn Ile Arg Met Lys Ala Glu Ser Glu Asn Ala Met
MGL1   Leu Ser Thr Leu Asn Ile Arg Met Lys Ala Glu Ser Glu Asn Ala Met
                   260                 265                 270
AC2-1  Lys Val Ala Glu Tyr Leu Lys Ser His Pro Ala Val Glu Lys Val Tyr
MGL1   Lys Val Ala Glu Tyr Leu Lys Ser His Pro Ala Val Glu Lys Val Tyr
               275                 280                 285
AC2-1  Tyr Pro Gly Phe Glu Asp His Glu Gly His Asp Ile Ala Lys Lys Gln
MGL1   Tyr Pro Gly Phe Glu Asp His Glu Gly His Asp Ile Ala Lys Lys Gln
               290                 295                 300
AC2-1  Met Arg Met Tyr Gly Ser Met Ile Thr Phe Ile Leu Lys Ser Gly Phe
MGL1   Met Arg Met Ser Gly Ser Met Ile Thr Phe Ile Leu Lys Ser Gly Phe
               305                 310                 315             320
AC2-1  Glu Gly Ala Lys Lys Leu Leu Asp Asn Leu Lys Leu Ile Thr Leu Ala
MGL1   Glu Gly Ala Lys Lys Leu Leu Asp Asn Leu Lys Leu Ile Thr Leu Ala
                       325                 330                 335
AC2-1  Val Ser Leu Gly Gly Cys Glu Ser Leu Ile Gln His Pro Ala Ser Met
MGL1   Val Ser Leu Gly Gly Cys Glu Ser Leu Ile Gln His Pro Ala Ser Met
                   340                 345                 350
AC2-1  Thr His Ala Val Val Pro Lys Glu Glu Arg Glu Ala Ala Gly Ile Thr
MGL1   Thr His Ala Val Val Pro Lys Glu Glu Arg Glu Ala Ala Gly Ile Thr
               355                 360                 365
AC2-1  Asp Gly Met Ile Arg Leu Ser Val Gly Ile Glu Asp Ala Asp Glu Leu
MGL1   Asp Gly Met Ile Arg Leu Ser Val Gly Ile Glu Asp Ala Asp Glu Leu
               370                 375                 380
AC2-1  Ile Ala Asp Phe Lys Gln Gly Leu Asp Ala Leu Leu
MGL1   Ile Ala Asp Phe Lys Gln Gly Leu Asp Ala Leu Leu
               385                 390             395
```

*FIG. 1B*

HIGH SPECIFICITY HOMOCYSTEINASES

This application is a continuation-in-part of U.S. application Ser. No. 09/340,991, filed Jun. 28, 1999 now U.S. Pat. No. 6,066,467 which is a continuation-in-part of U.S. application Ser. No. 09/122,129, filed Jul. 24, 1998 now U.S. Pat. No. 5,998,191, which is a continuation-in-part of U.S. application Ser. No. 09/061,337, filed Apr. 17, 1998 now U.S. Pat. No. 5,985,540, which is a continuation-in-part of U.S. application Ser. No. 08/974,609, filed Nov. 19, 1997 now U.S. Pat. No. 6,140,102, which is a continuation-in-part of Ser. No. 08/941,921, filed on Oct. 1, 1997 now abn., a continuation-in-part of U.S. application Ser. No. 08/918,214, filed on Aug. 25, 1997 now abn., which is a continuation-in-part of U.S. application Ser. No. 08/899,776, filed on Jul. 24, 1997 now abn., and each incorporated by reference herein, in its entirety, as if fully set forth. Priority is claimed under 35USC 120.

FIELD OF THE INVENTION

The invention relates to homocycsteinase enzymes that have a high level of specificity for homocycsteine as opposed to cycsteine. The invention also relates to enzyme preparations that comprise one or more homocysteinase enzymes and diagnostic kits containing these enzymes. Because of the high specificity of the homocycsteinase, hydrogen sulfide evolution can be used as a measure of the amount of homocysteine present. However, in addition, or in the alternative, the production of α-ketobutyrate which is the product of homocysteine lysis can be used as a measure of the amount of homocysteine originally present.

BACKGROUND ART

As disclosed in PCT publication WO99/05311, published Feb. 4, 1999, and incorporated herein by reference, there is justified clinical interest in measuring the levels of blood plasma homocysteine due to the correlation of elevated plasma homocysteine concentrations and arteriosclerotic disease. Because of this interest and the diagnostic value of homocysteine levels as an indicator of cardiovascular condition and prognosis, improved methods for making this assessment are desirable. Further, our simplicity in such assays is a highly desirable characteristic. The present invention relates to an aspect of these assays in which resides the use of homocysteinases with improved specificity for homocysteine in comparison to cysteine.

"Homocysteinase" refers to a desulfurase that decomposes homocysteine to yield hydrogen sulfide, ammonia, and α-ketobutyrate. Homocysteinases are generally not completely specific for homocysteine and also decompose cysteine to obtain hydrogen sulfide, ammonia, and α-ketopropionate. In addition, normal levels of cysteine in blood plasma are considerably higher than those of homocysteine. The normal range of cysteine levels is about 30–120μ molar and those of homocysteine only about 5–15μ molar. Thus, if homocysteine content is to be measured by treating plasma with homocysteinase and measuring the common product hydrogen sulfide (or ammonia), the homocysteinase must be sufficiently specific for homocysteine in contrast to cysteine to provide an accurate measurement without interference from the cysteine levels. The present invention provides such homocysteinase enzymes.

In prior assays which have involved the use of homocysteinase and detection of hydrogen sulfide, such as that described by Thong, K. W., et al., *Experimental Parasitology* (1987) 63:143–151; Thong, K-W, et al., *IRCS Medical Science* (1985) 13:493–496, interference by the cysteine present was observed. In the case of the homocysteinases of the present invention, a sufficiently catalytic ability with respect to cysteine is achieved that an accurate measure of homocysteine in plasma can be directly obtained in a single enzyme assay using hydrogen sulfide as the detected product.

DISCLOSURE OF THE INVENTION

The present invention provides methods to determine the concentration of homocysteine in biological fluids, such as urine, tissue fluid, blood, blood serum, or blood plasma sample from a patient. These methods are useful to assess risk for cardiovascular disease. The methods determine homocysteine concentrations in biological fluids while avoiding detection of related but interfering substances, most particularly cysteine and methionine. The present invention achieves this by providing homocysteinase enzymes of sufficient specificity.

In one aspect, the invention is directed to a homocysteinase which is sufficiently specific for homocysteine as compared to its ability to decompose cysteine to provide a valid measure of homocysteine in a biological fluid even in the presence of normal amounts of cysteine. Preferably, the homocysteinase of the invention has the property such that at least about 90% of the hydrogen sulfide produced by action of said homocysteinase upon contacting a biological fluid is contributed by homocysteine when the concentrations of homocysteine and cysteine in the fluid are, respectively, about 5–15μ molar and about 100–300μ molar. Preferably, under these conditions, at least about 99% of the hydrogen sulfide produced by said homocysteinase is contributed by homocysteine. The invention also includes recombinant materials and methods to prepare the homocysteinase of the specificity required by the present invention.

Accordingly, there is provided a method for determining the amount of homocysteine that is present in a biological sample containing, for example, homocysteine and cysteine, that comprises contacting said sample with an enzyme preparation that produces hydrogen sulfide from homocysteine and determining the amount of homocysteine in said sample by measuring the amount of hydrogen sulfide produced from homocysteine. The enzyme preparation consists only of one or more enzymes whose reactivity toward homocysteine is sufficient, compared to cysteine, that hydrogen sulfide produced from cysteine may be ignored. Alternatively, α-ketobutyrate may be measured as a correlate to homocysteine levels.

Said enzyme preparation comprises an enzyme referred to as a homocysteinase, and which may also be referred to by other names as described below. Additionally, the term "enzyme preparation" should also be understood to include, unless otherwise noted, both a single and a plurality of aliquots, that is, either a single amount or multiple amounts of one or more enzymes may be added during the course of an assay procedure, and the use of the term is without limitation has to how, or how many, aliquots or steps are used to add all of the necessary enzymes during an assay.

According to a preferred aspect of the invention, it is recognized that the total concentration of homocysteine present in biological samples, for example in body fluids, includes homocysteine molecules that are not present in free form, being instead covalently coupled to other molecules. The methods of the invention provide further steps for releasing this homocysteine prior to measuring of homocysteine-derived hydrogen sulfide.

It should be noted, however, that since the methodology of the present invention provides for accurate measurement of free homocysteine levels absent interference from related substances (for example, cysteine), valuable information is provided to the clinician even if only free homocysteine is detected. Among many uses, it is expected that such information is very useful as a fast initial diagnostic tool, for example, in the testing of all newborn infants.

In one preferred embodiment, the homocysteinase is a natively produced homocysteinase which has optionally been mutated to enhance its specificity. Techniques are described below whereby such mutations can be randomly generated and readily screened to select for those which result in homocysteinases of the required specificity.

In another preferred embodiment, the nucleotide sequence encoding the homocysteinase is derived from more than one gene or other polynucleotide that encodes a homocysteinase, wherein expression of such sequence leads to the production of a chimeric homocysteinase. A preferred example includes a chimeric enzyme that comprises amino acid sequences derived from both *Trichomonas vaginalis* and *Pseudomonas putida* homocysteinase.

Thus, the homocysteinase enzyme of the invention is sufficiently non-reactive toward cysteine or methionine that the concentration of homocysteine that is present, for example, in a sample of tissue fluid, urine, blood, blood serum, or blood plasma of a subject may be determined in a single step assay, wherein is measured the amount of one or more products resulting from reaction of said homocysteinase on homocysteine in said sample, and wherein said measurement is substantially unaffected by the concentration of cysteine or methionine therein.

In a particularly preferred embodiment the homocysteinase is a substitution variant, addition variant, deletion variant, or derivative of SEQ ID NO: 10, wherein said variant or derivative has one or both of the following properties:
  (a) at least about 110% of the activity of SEQ ID NO: 10 toward homocysteine in a suitable assay; and/or
  (b) no more than about 90% of the activity of SEQ ID NO: 10 toward cysteine (or methionine) in a suitable assay.

For the clinical practice of the invention, there is provided a diagnostic kit for use in determining the amount of homocysteine in a biological sample, and wherein the homocysteinase included therewith as described below. In a preferred embodiment, the diagnostic kit comprises (a) a homocysteinase of the required specificity, e.g., derived from that of *Trichomonas vaginalis,* or Pseudomonas (such as species ovalis or putida), and (b) at least one reagent capable of being used to determine the amount of hydrogen sulfide formed in the homocysteinase reaction.

BRIEF DESCRIPTION OF THE DRAWINGS

FIG. 1 (panels A and B) provides a comparison of the amino acid sequence of *Trichomonas vaginalis* homocysteinase encoded by the mgl1 gene with that encoded by the *Trichomonas vaginalis* pAC2-1 clone.

MODES OF CARRYING OUT THE INVENTION

Figure 2:
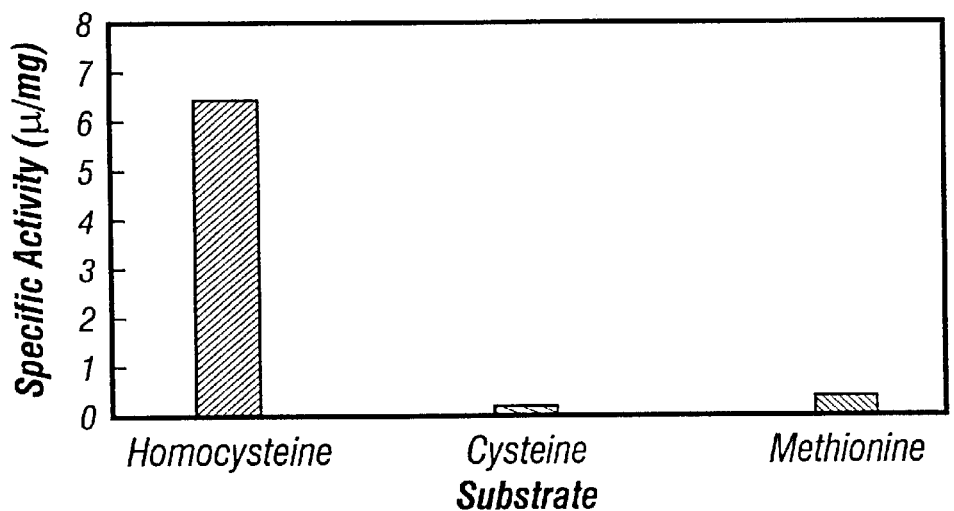
FIG. 2 shows the comparative specific activities (units/mg crude *E. coli* extract) corresponding to homocysteinase of the pAC2-1 clone for cysteine, methionine, and homocysteine.

Elevated blood plasma homocysteine levels are recognized as a risk factor for vascular disease. The atherogenic properties of homocysteine were first noted in association with a rare group of genetic diseases referred to collectively as homocystinuria. The disease state is characterized by a level of circulating homocysteine that is typically 10-fold (or greater) above that in normal blood. Under these circumstances, homocysteine is also detected in the urine. Premature vascular disease is strongly correlated with this condition.

According to the practice of the invention, homocysteine concentrations in biological samples are determined enzymatically with enzymes hereinafter referred to as "homocysteinase", which are defined as enzymes capable of catalyzing reactions whereby hydrogen sulfide is produced from homocysteine. In the typical case, ammonia and α-ketobutyrate are also produced. As described herein, it is preferred to detect product hydrogen sulfide, although product ammonia and/or α-ketobutyrate or other products may also be detected. Homocysteinases, as defined herein, may catalyze other reactions involving other sulfhydryl compounds and have acquired multiple names in the literature; however, they are generally useful in the practice of the present invention if they possess the property of catalyzing production of hydrogen sulfide from homocysteine.

The said homocysteinase of the invention is sufficiently non-reactive toward cysteine that any hydrogen sulfide produced by reaction of said homocysteinase on cysteine does not substantially interfere with the use of said kit to assess risk for cardiovascular disease.

The homocysteinase has the property that at least about 90% of the hydrogen sulfide produced by action of said homocysteinase upon contacting a biological sample in an assay for homocysteine is contributed by said homocysteine when, for example, the concentrations of homocysteine and cysteine in said fluid are, respectively, about 5–15μ molar and about 100–300μ molar, preferably when the homocysteine concentration is 5 μM and that of cysteine is 300 μM. Preferably, the included homocysteinase has the property that at least about 99% of the hydrogen sulfide produced by action of said homocysteinase upon contacting said biological fluid under either of the above conditions is contributed from homocysteine. Such diagnostic kits can be used, for example, to accurately determine the homocysteine concentration in biological fluids in the range of about 1–500μ molar, or higher as necessary, wherein said fluids also contain from 0 to about 1000μ molar of cysteine, in a typical example.

With respect to the other assay procedures using the homocysteinase of the invention, it is generally preferred to include use of a disulfide reducing agent, such as dithiothreitol ("DTT"), so that homocysteine molecules in biological samples that are disulfide-bonded to other molecules (such as free cysteine, other homocysteine molecules or protein SH groups) can also be detected.

A homocysteinase that has previously been isolated is L-methionine-alpha-deamino-gamma-mercaptomethane lyase (methionine lyase) derived from the bacterial source, *Pseudomonas putida*. The enzyme has been purified by S. Ito et al., *Journal of Biochemistry*, (1976) 79:1263–1272, and determined to have a molecular weight of about 170 kDa. In the context studied by Ito, the enzyme carried out the alpha-gamma elimination of methionine to α-keto butyrate, methanethiol, and ammonia, but it also converts homocysteine α-keto butyrate, hydrogen sulfide, and ammonia. The homologous enzyme has been isolated from *Pseudomonas ovalis*, H. Tanaka, et al., *Biochemistry*, (1977) 16;100–106. Methods for the recombinant production of this Pseudomonas enzyme have also been developed (see Tan, Y., et al., *Protein Expression and Purification*, (1997) 9;233–245.

The substrate specificity of the *P. putida* enzyme has also been determined. For example, Esaki, N., et al. *Methods in Enzymology*, (1987) 143;459–465 report that on a relative activity scale where activity toward methionine is assigned 100, cysteine is 10, and homocysteine is 180. The apparent 10-fold preference of the enzyme for homocysteine over cysteine does not take into account that the concentration of cysteine in a biological sample is generally much higher than the concentration of homocysteine. Homocysteinase enzymes of suitable catalytic activity for use as starting materials to obtain mutated forms can be derived from other Pseudomonas species, or from other bacteria, using routine screening procedures and assays that are recognized in the art.

An additional group of organisms that are a source of homocysteinase are species of the Trichomonad parasites and related protozoans. Trichomonads are important parasites of the urogenital tract and are aerotolerant (but nonetheless anaerobic) flagellate protozoa. Use of homocysteinase from *Trichomonas vaginalis* is a preferred embodiment.

Trichomonas species are believed to use their capabilities for thiol metabolism in order to counter oxygen toxicity in host tissues, see K-W Thong et al., *Experimental Parasitology*, (1987) 63;143–151 , and papers cited therein. Although considerable variation in homocysteinase activity (termed homocysteine desulfurase activity therein) was found between Trichomonas species, it is routine to screen available species for acceptable levels of enzyme activity. Generally speaking, it is preferred that a homocysteinase should have a specific activity of at least about 1 unit/mg purified protein, although it is well within the skill of those familiar with the relevant art to design variations on assays that use greater or lesser amounts of enzyme or enzyme preparations with differing enzyme activity. It is noted that highly purified and active *P. putida* enzyme has a specific activity of about 20 units/mg (a unit of enzyme activity may be described as 1 micromole of substrate converted per minute under standard conditions (see Y. Tan et al. above).

The "homocysteine desulfurase activity" reported by K-W. Thong et al. (1987) above appears to result from the same enzyme responsible for methionine catabolizing activity in Trichomonas, and later termed methionine-gamma-lyase by B. C. Lockwood and G. H. Coombs (*Biochemical Journal*, (1991) 279;675–682, wherein is also described purification of this enzyme.

Use of a recombinant versions of enzymes is preferred. One potential cloning strategy follows the observations that *T. vaginalis* genes may have few introns. Accordingly, a genomic library would be constructed and screened with DNA fragments corresponding to the *Psuedomonas putida* enzyme, and which are expected to reflect some partially conserved sequence.

Lockwood et al. also list other reports of bacteria having methionine-gamma-lyase activity involving species of Pseudomonas, Clostridium, and Aeromonas.

It is expected that such species are sources of homocysteinase activity useful in the practice of the present invention. Additional organisms that are expected to provide useful homocysteinase enzymes are certain marine algae (see, for example, D. A. Gage, et al., *Nature*, (1997) 387;891–897, describing species with extensive methionine-related metabolism); sulfur bacteria; and geomicrobes or other microbes living under extreme environmental conditions (see, for example, R. A. Kerr, *Science*, (1997) 276;703–704, and E. Pennist, *Science*, (1997) 276;705–706,. Additional examples of microorganisms that may be useful sources for homocysteinase-type enzymes include bacteria involved in periodontal disease, such as are capable of forming volatile sulfur compounds from cysteine. In this regard, see S. Persson et al., *Oral Microbiology and Immunology*, (1990) 5(4);195–201.

Finally, with respect to the definition of "homocysteinases" that are useful in the assessment of homocysteine in biological fluids, it should not be viewed as a limitation that hydrogen sulfide necessarily be a product of such enzymes. Broadly speaking, the present invention provides for high through-put diagnostic procedures, permitting the cost effective analysis of a very large number of homocysteine-containing samples while avoiding detection of interfering substances.

Accordingly, it is expected that other enzymes that metabolize homocysteine are useful in the practice of the invention if methods exist to detect such metabolites under conditions where interference from substances similar to homocysteine (such as cysteine) can be avoided. The following examples describe a considerable spectrum of techniques to measure homocysteine while avoiding detection of interfering substances. Accordingly, it will be appreciated that the techniques disclosed below can be adapted by those skilled in the art to detection methods using many other enzymes that act on homocysteine.

As will be described below, naturally occurring homocysteinases with promising specificity ratios may serve as useful starting materials for generating mutant or "mutated forms" thereof. By a "mutated form" of a homocysteinase, is meant a homocysteinase which is at least about 70%, more preferably 80%, and most preferably 90% homologous with a homocysteinase that occurs in nature and has been identified in a particular organism. Of course, the mutations are generally achieved by mutating the gene, but the homology requirements set forth above are with respect to the reduced amino acid sequences.

Thus, in addition to obtaining appropriate homocysteinases by or retrieving the genes encoding these proteins from host organisms such as those set forth above or additional organisms harboring such enzymes and producing the enzymes recombinantly, or simply purifying homocycteinases from these organisms combined with assaying their specificity, techniques are available for rapidly screening mutated forms of the genes encoding these enzymes to retrieve mutated genes which have the appropriate specificity. Since hydrogen sulfide is produced by lysis both of homocysteine and cysteine, comparative identically assayed cultures fed each of these amino acids can be used to determine specificity. The degree of specificity can be set arbitrarily by controlling the concentration of cysteine or homocysteine fed.

By way of example, the gene encoding homocysteinase from *P. putida,* for example, or from a comparable organism can be ligated into an appropriate expression vector and colonies producing the homocysteinase protein cultured. Either homocysteine or cysteine is fed at the desired concentration to each of the two matching cultures of such an organism. Cysteine is added to one portion and homocysteine to the other. At appropriate times, the cultures are contacted, with, for example, lead acetate or other substance which reacts with hydrogen sulfide to generate a detectable resultant. Colonies which show a high reactivity when fed homocysteine, but which show essentially undetectable activity or very low detectability when fed cysteine have the appropriate specificity.

The appropriate choice of production colony can then be confirmed by isolating the homocysteinase from this organism and comparing the activity with respect to homocysteine and cysteine in separate in vitro assays or in systematically combined assays. In this way, a definite ratio of reactivities can be obtained. In addition, the isolated enzyme or culture medium can be used in a homocysteine assay in plasma, optionally with cysteine spiking, to determine the appropriate specificity. Thus, the criterion selected above—that about 90% of the hydrogen sulfide produced by reaction of the homocysteinase on contacting a biological fluid is contributed by a homocysteine when the concentrations of homocysteine and cysteine are respectively about 5–15$\mu$ molar and about 100–300$\mu$ molar can be confirmed.

In addition, mutations may be introduced systematically into a native sequence by manipulating the gene in a prescribed manner. That is, the genetic manipulations can be such that particular identified changes are made in the resulting protein. Screening for success in these cases can be done in a manner similar to that set forth above, or any other convenient protocol.

Thus, starting with a naturally occurring homocysteinase that has a satisfactory specificity, for example, one where the activity with respect to homocysteine is ten times or more greater than with respect to cysteine, mutants can be selected wherein mutant has at least about 110%, preferably about 125%, and more preferably at least 150% at the activity of the starting out native homocysteinase toward homocysteine and/or no more than 90%, preferably less than 80% and more preferably less than 60% of the activity of the starting homocysteinase toward cysteine or methionine in the same assay.

The activity of the novel *Trichomonas vaginalis* homocysteinase represented by SEQ ID NO: 10 is of particular note. The relative activity of this enzyme even in unmutated form toward homocysteine, compared to cysteine, will readily permit homocysteine measurements without the need to correct for any cysteine present in the biological test sample.

In a preferred example of the invention, novel enzymes are patterned on homocysteinases found in various microorganisms including Pseudomonas, Clostridium, Aeromonas or Trichomonas, and particularly preferred homocysteinases are derived from *T. vaginalis,* including that expressed from the mgl1 gene (SEQ ID NO: 11), or the mgl2 gene thereof.

In FIG. 1 (panels A and B) are depicted the amino acid sequences of two *Trichomonas vaginalis* homocysteinases, the first derived from a novel clone (pAC2-1) of the present invention, and the second, the enzyme derived from the known mgl1 gene (see also SEQ ID NOS: 10 and 12 for comparison of amino acids; SEQ ID NOS: 9 and 11 for comparison of encoding DNA's). It will be seen that pAC2-1 is characterized by the existence of three differences (mutations), compared to mgl1:

Phe to Leu at amino acid position 47,

Asp to Glu at amino acid position 172, and

Ser to Tyr at amino acid position 308.

Modified homocysteinase amino acid sequences, made by incorporating amino acid substitutions that include one or more of these differences (mutations), are particularly useful in the practice of the invention. Accordingly, a preferred example of the invention involves providing a homocysteinase to contain one or more peptide (sub)sequences of SEQ ID NO: 10 that are selected from the group consisting of:

(a) Gly-Gly-Asn-Arg-Leu-Ala-Gly-Gln-Glu, (see residues 43–51 of SEQ ID NO: 10);

(b) a subset of (a) that comprises Leu;

(c) Arg-Val-Cys-Lys-Glu-Ala-His-Ser-Gln, (see residues 168–176 of SEQ ID NO: 10);

(d) a subset of (c) that comprises Glu;

(e) Gln-Met-Arg-Met-Tyr-Gly-Ser-Met-Ile; (see residues 304–312 of SEQ ID NO: 10); and (f) a subset of (e) that comprises Tyr.

It should also be noted that SEQ ID NO: 10, a preferred homocysteinase of the invention, is expressed from a DNA sequence (pAC2-1, see SEQ ID NO: 9) isolated as a gene from *Trichomonas vaginalis* genomic DNA. In contrast, the reported isolation of mgl1 and mgl2 appears to have involved a cDNA procedure. pAC2-1 may thus represent a new homocysteinase Trichomonas gene.

In a representative example, the homocysteinase is patterned on an enzyme from Pseudomonas, Clostridium, Aeromonas or Trichomonas wherein one or more peptide (sub) sequences of the original polypeptide sequence(s) thereof are correspondingly replaced by one or more corresponding peptide sequences of SEQ ID NO: 10 that are selected from the group consisting of:

(a) Gly-Gly-Asn-Arg-Leu-Ala-Gly-Gln-Glu, (see residues 43–51 of SEQ ID NO: 10);

(b) a subset of (a) that comprises Leu;

(c) Arg-Val-Cys-Lys-Glu-Ala-His-Ser-Gln, (see residues 168–176 of SEQ ID NO: 10);

(d) a subset of (c) that comprises Glu;

(e) Gln-Met-Arg-Met-Tyr-Gly-Ser-Met-Ile, (see residues 304–312 of SEQ ID NO: 10); and (f) a subset of (e) that comprises Tyr.

In this regard, use of the term "corresponding" is not intended to suggest that homology is exact, but rather, that a comparison of such sequences using generally recognized models would suggest that such sequences, even if now significantly different, may have evolved from a common ancestor gene or subset thereof. Similarly, the term "mutation" as used herein, should be broadly understood to include modifications that arise by whatever means, whether natural, or experimental and the like.

Accordingly, a generally preferred example includes a chimeric homocysteinase patterned on a first Trichomonas homocysteinase wherein one or more amino acids thereof, that correspond to the Leu$^{47}$, Glu$^{172}$, and Tyr$^{308}$ residues of a second Trichomonas homocysteinase (that from pAC2-1, as depicted in SEQ ID NO: 10), are correspondingly replaced by one or more of said Leu$^{47}$, Glu$^{172}$, and Tyr$^{308}$.

Successful variants include a homocysteinase that is a substitution variant, addition variant, deletion variant, or other derivative of SEQ ID NO: 10, wherein said variant or derivative has one or both of the following properties:

(a) at least about 110%, preferably about 125%, more preferably at least 150% of the activity of SEQ ID NO: 10 toward homocysteine in a suitable assay; and/or (b) no more than about 90%, preferably less than 80%, more preferably less than 50% of the activity of SEQ ID NO: 10 toward cysteine or methionine in a suitable assay.

Also included among successful variants are those that have somewhat decreased specificity with regard to that exhibited by SEQ ID NO: 10. Thus, the appropriate specificity can be maintained even though the activity of the homocysteinase mutated form is reduced to 50% of the activity of SEQ ID NO: 10 in a suitable assay and the activity with respect to cysteine is increased twofold with respect to cysteine.

Such a range of properties is generally believed to maintain sufficiently enhanced activity of the enzyme with respect to homocysteine, in comparison with cysteine or methionine, that single step methodology is still practical, although it will be appreciated that the exact requirements for such relative sensitivity may be readily determined in each clinical application. For example, cysteine would generally be expected to be at low concentration in a urine sample, at least with respect to a non-diseased patient. With respect to the provision of mutant homocysteinases from other organisms, as produced for example by appropriate recombinant methods, the above relative guidelines are expected to prove useful. The enzyme represented by SEQ ID NO: 10 is a particularly useful example given that the apparent activity of this homocysteinase for homocysteine is at least about 100-fold greater than for cysteine and methionine.

In a representative example whereby a homocysteinase is modified to improve its usefulness for single-step assay methodology, the wild type *T. vaginalis* amino acid sequence (from mgl1, see SEQ ID NOS: 11 and 12) is altered (generally of course by modification of an appropriate encoding DNA) as follows:
one or more of $Phe^{47}$, $Asp^{172}$, and $Ser^{308}$ thereof is deleted, or is replaced according to the following formula:

(1) for $Phe^{47}$, replaced with Leu, Ile, Val, Ala, Gly, Met, and Trp;

(2) for $Asp^{172}$, replaced with Glu, Gln, or Asn;

(3) for $Ser^{308}$, replaced with Tyr, Phe, Met, Trp, Gln, Thr, or Asn, wherein are suggested relatively conservative amino acid substitutions, as is recognized in the art, and whose efficacy in this regard can be determined by routine experimentation.

Alternatively a chimeric nucleotide sequence (whether of DNA or RNA), derived from more than one gene (or other polynucleotide such as a cDNA or other intron-less sequence), that codes for a chimeric homocysteinase enzyme can be constructed. A preferred example encodes a chimeric enzyme that comprises amino acid sequences corresponding to both *Trichomonas vaginalis* and *Pseudomonas putida* homocysteinases.

It is believed that *P. putida* homocysteinase is more stable than the *T. vaginalis* enzyme under a variety of conditions. As one probable consequence thereof (see B. Lockwood et al., *Biochemical Journal*, (1991) 279;675–682, recovery of the *T. vaginalis* enzyme during purification was very low (see p. 679 at Table 2, referring to "methionine γ lyase"). Thus it is preferred to include *P. putida* sequences in chimeric enzymes in order to take advantage of this enhanced stability. On the other hand, the *T. vaginalis* enzyme has a higher reactivity toward homocysteine as substrate than does the *P. putida* enzyme, which may show greater reactivity toward cysteine, or methionine as substrate. In this regard, the results reported by Lockwood et al., 1991 at Table 4 thereof) are of note in that relative activity data for the *T. vaginalis* enzyme evidence a very pronounced "preference" for homocysteine as substrate (see also the $K_m$ data reported on page 678 thereof). This is in contrast to the data reported by N. Esaki et al. above with respect to the *P. putida* enzyme.

*T. vaginalis* homocysteinase actually represents two protein species derived from two genes (see J. C. Mottram, direct submission of sequences to Gene Bank, submitted Jul. 17, 1997, as *T. vaginalis* mgl1 gene, accession number AJ000486, NID g2330884, and *T. vaginalis* mgl2 gene, accession number AJ000487, NID g2330886), the complete sequences of which are fully incorporated by reference herein, as if directly set forth. See also International Patent application WO 98/07872 published Feb. 26, 1998, and A. McKie et al., *Journal of Biological Chemistry*, (1998) 278;5549–5556,.

The present invention therefore provides for a purified and isolated DNA molecule comprising a chimeric nucleotide sequence that encodes amino acid sequence of *Pseudomonas putida* homocysteinase, and amino acid sequence of *Trichomonas vaginalis* homocysteinase (derived from either mgl1, or mgl2, or both) from which can be expressed a functional protein having homocysteinase activity. In a preferred aspect, the nucleotide construct (or corresponding amino acid construct) corresponds predominantly to that of *P. putida,* and thus there is provided a DNA molecule that comprises an encoding nucleotide sequence for *Pseudomonas putida* homocysteinase, wherein one or more subsequences thereof that encode one or more amino acids of said enzyme are correspondingly replaced by one or more nucleotide subsequences that encode the corresponding amino acids of a *Trichomonas vaginalis* homocysteinase. In the practice of the present invention, the *T. vaginalis* enzyme encoded by the mgl1 gene is hereinafter referred to as the T1 protein, and that encoded by the mgl2 gene is referred to as the T2 protein.

In connection with the selection of chimeric polypeptides and encoding polynucleotides, the following considerations are of note. The T1 and T2 proteins are encoded by remarkably similar DNA sequences. Accordingly, it is generally expected to be the case that substitution of an mgl1-encoding subsequence into a *P. putida* backbone will have substantially the same effect, and generate improvements substantially similar to those resultant from an equivalent mgl2 subsequence substitution.

However, it is noted that there are a limited number of subregions where the T1 and T2 sequences differ substantially, while at the same time, the T1 sequence (less so the T2 sequence) shows substantial homology with the published *P. putida* sequence. Indeed, the published *P. putida* sequence shows considerable homology with the T1 sequence.

Thus, in a further preferred aspect of the invention, there are identified regions of the encoding sequence for *T. vaginalis* enzyme where the T2 sequence and corresponding T1 sequence are very different from each other, and yet the T1 sequence is substantially similar to that of *P. putida*. Without being limited as to theory, it is believed that these encoding subregions of T2 present unique opportunities to insert into the a *P. putida* encoding polynucleotide, amino acid sequence domains that provide enhanced reactivity of the chimeric species toward homocysteine, thereby facilitating the diagnostic procedures of the invention.

The invention therefore provides for a DNA molecule that comprises an encoding sequence for *Pseudomonas putida* homocysteinase, wherein one or more subsequences thereof, that each encode one or more amino acids of said enzyme, are correspondingly replaced by one or more nucleotide subsequences than each encode the one or more corresponding amino acids of a *Trichomonas vaginalis* homocysteinase, and wherein said resultant amino acid replacements are selected from the group consisting of:

(a) Cys-Ser-Arg-Ala-Asp-Ile-Ile-Ala-Lys-Val-Lys-Ser (SEQ ID NO: 1), or any subset thereof, from *Trichomonas vaginalis* (T2) for Val-Gly-Ser-Gln-Ala-Leu-Val-Asp-Arg-Ile-Arg-Leu (SEQ ID NO: 2), or any subset thereof, from *Pseudomonas putida;*

(b) Asp-Val-Asp (SEQ ID NO: 3), or any subset thereof, from *Trichomonas vaginalis* (T2) for Glu-Leu-Lys (SEQ ID NO: 4), or any subset thereof, from *Pseudomonas putida;*

(c) Cys-His-Val-Val (SEQ ID NO: 5), or any subset thereof, from *Trichomonas vaginalis* (T2) for Ala-Leu-Gln-Leu (SEQ ID NO: 6), or any subset thereof, from *Pseudomonas putida;*

(d) Cys-Glu-Asn-Val-Gln-Asp-Ile-Ile-Asp-Asp (SEQ ID NO: 7), or any subset thereof, from *Trichomonas vaginalis* (T2) for Gly-Leu-Glu-Asp-Ile-Asp-Asp-Leu-Leu-Ala (SEQ ID NO: 8), or any subset thereof, from *Pseudomonas putida;* and (e) any combination involving one, two, three or four of the replacements provided for by groups (a), (b), (c), and (d) above.

With respect to the above-listed *Trichomonas vaginalis* mgl2 ("T2") amino acid subsequences it should be noted they correspond approximately to the following amino acid sequence positions:

Cys-Ser-Arg-Ala-Asp-Ile-Ile-Ala-Lys-Val-Lys-Ser (SEQ ID NO: 1), approximately 226–237;

Asp-Val-Asp (SEQ ID NO: 3), approximately 318–320;

Cys-His-Val-Val (SEQ ID NO: 5), approximately 331–335; and

Cys-Glu-Asn-Val-Gln-Asp-Ile-Ile-Asp-Asp (SEQ ID NO: 7), approximately 381–390.

In connection with the practice of this aspect of the invention, the above-listed *T. vaginalis* subsequences can be additionally modified to accept conservative amino acid substitutions. Additionally, the *T. vaginalis* subsequences need not correspondingly replace the above listed *P. putida* sequences so that, for example, the *T. vaginalis* subsequences may be inserted nearby (i.e. up to about 10 amino acid positions distant therefrom), while the targeted *P. putida* sequences remaining in place, in whole or in part. Additionally, the *T. vaginalis* inserts may comprise transfer of additional amino acids found on the N-terminal or C-terminal side of the above-depicted sequences thereof, as long as the benefit of increased reactivity toward homocysteine is not compromised owing to decreased enzyme stability.

In all of the above described modified homocysteinases, natives homocysteinases, and mutated forms of native homocysteinases, the encoding genes can be manipulated to effect more convenient purification, for example, by providing N-terminal histidine residues.

Nickel-NTA affinity purification procedures (available from the Qiagen Company, Germany) can be used to facilitate purification of homocysteinase from *E. coli* or other host cells transfected with an appropriate homocysteinase-encoding DNA sequence. These procedures take advantage of the selective binding of protein imidazole groups to nickel actions immobilized in the NTA resin matrix. In a preferred example of this aspect of the invention, by modification of an appropriate encoding DNA (see SEQ ID NOS: 9 and 10), an amino terminal tag that contains, for example, 6 consecutive histidine residues is introduced into the homocysteinase, thereby facilitating its purification from host cell materials.

Homocysteinase SEQ ID NO: 10 (see also FIG. 1AB), is representative of modified homocysteinase enzymes that comprise one or more histidine residues positioned upstream of the N-terminus of said proteins, said modified enzymes being sufficiently non reactive toward cysteine or methionine that the concentration of homocysteine that is present in a sample of tissue fluid, urine, blood, blood serum, or blood plasma of a subject may be determined by use of such enzymes in a single step assay. In such an assay, the amount of one or more products resulting from reaction of said modified homocysteinase on homocysteine are measured, and such measurements are substantially unaffected by the concentration of cysteine or methionine in the sample. According to this aspect of the disclosure, a homocysteinase that is useful in the practice of the invention comprises one or more, preferably 2–15, and most preferably 5–8 histidine residues consecutively positioned on the N-terminal side of the natural homocysteinase.

The construction of appropriate encoding polynucleotides is straightforward for those familiar with the art, and may involve techniques of site directed or loop out mutagenesis, or use of PCR technology. Appropriate host cells for the expression of such encoding polynucleotides are described, for example, in Y. Tan, et al., *Protein Expression and Purification,* (1997) 9;233–245. It is well within ordinary skill, once the appropriate genes have been constructed, to provide appropriate expression vectors or plasmids, or alternatively, to effect integration of the coding sequences, and if necessary, regulatory sequences or control sequences into the chromosome of a host organism. The parameters required for recombinant expression in a wide variety of hosts, including bacteria, yeast, mammalian cells, and plants is now well known in the art. Standard recombinant techniques can thus be employed to produce the homocysteinases of the invention once the desired encoding nucleotide sequences are available.

Assay Systems for Homocysteine

As stated above, the homocysteinases of the invention are useful in providing a component of a kit or otherwise employing such enzymes in single enzyme assays for homocysteine and body fluids, particularly in plasma, urine and the like. Specific exemplary species are set forth in the above noted U.S. Ser. No. 09/340,991 file Jun. 28, 1999, the parent application herein which is incorporated herein by reference. As a general matter, typically. In assay methods for homocysteine levels homocysteinase is added to a sample in an amount needed to achieve a final concentration of 0.01–1000 $\mu$g/ml; and reagents are added in amounts needed to achieve final concentrations of 1–100 mM of buffer, even more preferably 5–50 mM; 0.01–100 mM reducing agent, even more preferably 0.1–10 mM. The nature of the remaining reagents depends on the detection system chosen for the assay.

The following examples are meant to illustrate but not to limit the invention.

EXAMPLE 1

Production of the E. coli BL21 (DE3) pAC2-1 Clone

The cloning of the pAC2-1 homocysteinase gene of *Trichomonas vaginalis* was accomplished as described below. Generally speaking, recombinant methodology recognized as applicable in other microorganisms is useful with respect to manipulation of Trichomonas DNA, particularly so since many Trichomonas genes, as aforementioned, lack introns. Useful reference may therefore be made to Y. Tan et al., *Protein Expression and Purification*, (1997) 9:233–245, and International Patent publication number WO 96/40284 of Y. Tan et al., published Dec. 19, 1996.

Genomic DNA from *Trichomonas vaginalis* was isolated by standard procedures (Wizard Minipreps, Promega, Madison, Wis.), and used as a template for a PCR reaction conducted according to the method provided with a PCR reagent kit (Roche, Branchburg, N.J.). Oligonucleotide primers were developed based on the nucleotide sequence of the mgl1 gene (J. C. Mottram et al., Gene Bank, accession number AJ000486, NID g2330884, submitted Jul. 17, 1997).

The specific primers used were:
(sense)
5'-GGATTACATATGCATCATCATCATCATCACATGA GTGGCCACGCTATCGAC-3' (SEQ ID NO: 13), which includes a CATATG NdeI site; and (antisense) 5'-GGATTAGGATCCTTAGAGGACTAAGTCGAGAGCC-3' (SEQ ID NO: 14), which includes a GGATCC BamHI site. Additional reagents used included restriction endonucleases, T4 DNA ligase, and BL21(DE3) competent cells, all purchased from Stratagene (San Diego, Calif.). The GeneAmp PCR reagent kit was purchased from Roche (Branchburg, N.J.), and the DNA purification kit was purchased from Promega (Madison, Wis.). The oligonucleotide probes for PCR amplification were synthesized by IDT Inc. (Coralville, Iowa). All other reagents were purchased from Sigma (St. Louis, Mo.). Wild type *Trichomonas vaginalis* was purchased from the American Type Culture Collection (Rockville, Md.).

The PCR reaction conditions were as follows: 35 cycles of denaturation at 94° C. for 1 minute; annealing at 50° C. for 2 minutes; and extension at 72° C. for 2 minutes. This was followed by a final extension step at 72° C. for 10 minutes. The PCR-amplified product (which appeared as one band of 1.2K bp identified by Kb-ladder markers) was collected, digested with the NdeI and BamHI restriction enzymes, and then ligated into the pT7-7 vector at the NdeI and BamHI cloning sites thereof, using standard protocols (the pT7-7 vector was provided by Dr. Stan Tabor, Harvard Medical School, Boston, Mass., see Tabor, S. "Expression using the T7 RNA polymerase/promoter system," in *Current Protocols in Molecular Biology*, F. A. Ausubel, et al., eds., 1990, pp. 16.2.1–16.2.11, Greene Publishing and Wiley-Interscience, New York). The resulting plasmid was then transformed into *E. coli* BL21 (DE3) cells by electrotransformation.

After incubation at 37° C. overnight, ampicillin-resistance clones were selected from ampicillin-containing plates. The cells from the selected colonies were grown in 5 ml LB medium (Fisher) at 37° C. overnight. Suitable clones were selected based on enzyme activity of crude culture extracts in the α-ketobutyrate assay (using a modification of the method of K. Soda et al., *Methods in Enzymology*, 143, 459–465, 1981—based on reaction of methyl-2-benzothiazolinone hydrazone), and/or a dethiomethylation assay in which $H_2S$ is produced and quantified (see A. E. Braunstein, et al., *Biochimica et Biophysica Acta*, (1971) 242:247–260,, which are both recited directly below.

A variant of the *E. coli* BL21 (DE3) pAC2-1 clone was also constructed which differs only in that the included plasmid (expression vector pAC2-11, again based on pT7-7) contains two copies of the homocysteinase-encoding sequence, which are present in tandem. This particular clone, designated *E. coli* BL21 (DE3) pAC2-11 provides high level expression of recombinant homocysteinase for use in the diagnosis procedures of the invention. Briefly the 2 copies of the encoding sequence were placed between the NdeI and Bsp106I sites of pT7-7. The first copy was linked NdeI to BamHI, and the second was linked BamHI to Bsp106I. Recombinant homocysteinase may be purified from either the pAC2-1 or pAC2-11 clones by the same procedures.

The α-Ketobutryate/Pyruvate Assay

In the first step of this assay, 1 ml volumes of 100 mM phosphate buffer pH 8.0, containing also 10 μM pyridoxal phosphate, and different concentrations (25 μM–25 mM) of DL-homocysteine, or L-methionine, L-cysteine, respectively, were incubated, for 10 min at 37° C., with a sufficient sample (typically 50 μl) of crude cell extract (cells were sonicated, and the supernatant was recovered following centrifugation) to provide about 1–100 units of homocysteinase ("HCYase") enzyme. The reactions were stopped by adding 0.1 ml of 50% TCA. The suspensions were then centrifuged using an Eppendorf centrifuge at 13 k rpm for 2 minutes. 0.5 ml samples of the supernatants were then added to 0.5 ml of 0.05% 3-methyl-2-benzothiazolinone hydrazone ("MBTH") in 0.8 ml of 1M sodium acetate, pH 5.2 and incubated at 50° C. for 30 min. The amount of reaction products was determined for each sample, by spectrophotometry at $OD_{320}$. The amount of protein was determined with a Bio-Rad 500-0006 kit (Bio-Rad, Richmond, Calif.) with bovine serum albumin as a standard. The enzyme specific activity was calculated as units/mg protein, with one unit of enzyme defined as the amount that catalyzes the formation of 1 μmol of α-ketobutyrate from homocysteine per minute. The assay procedure can, of course, also be used with purified homocysteinase samples that provide, for example, 1–100 units of enzyme per assay test.

The Dethiomethylation Screening Assay

As aforementioned, the assay used was a modification of the method of A. E. Braunstein et al. above. The standard reaction mixture consisted of potassium phosphate buffer (pH 7.5, 100 mM), lead acetate (0.33 mM), and sufficient crude cell extract to provide 1–100 units of homocysteinase, to which mixture different concentrations (5 μM–100 μM) of substrate DL-homocysteine, or L-cysteine or L-methionine were added, such that the total reaction volume was 1.5 ml. After incubation at 37° C. for 10 min, the determination of lead sulfide was obtained on a spectrophotometer at $OD_{360}$. The assay procedure can also be used with purified homocysteinase samples, for example, those providing 1–100 units per assay test.

Purification of Product Homocysteinase

Figure 3:
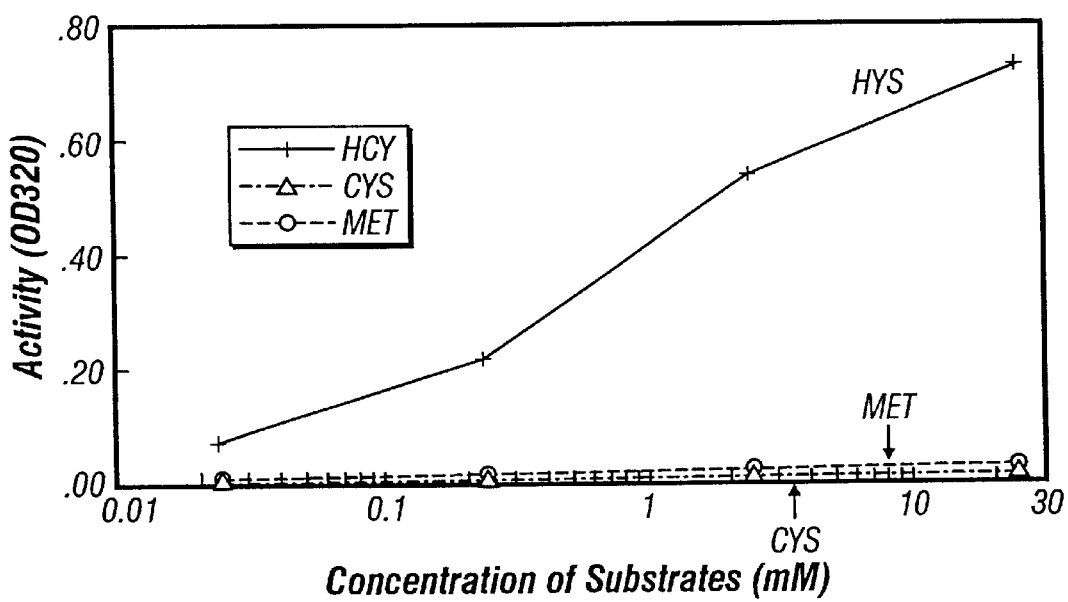
FIG. 3 shows the comparative specific activities of homocysteinase (pAC2-1 clone, purified using a DEAE-Fast Flow procedure) for cysteine, methionine, and homocysteine.
Figure 4:
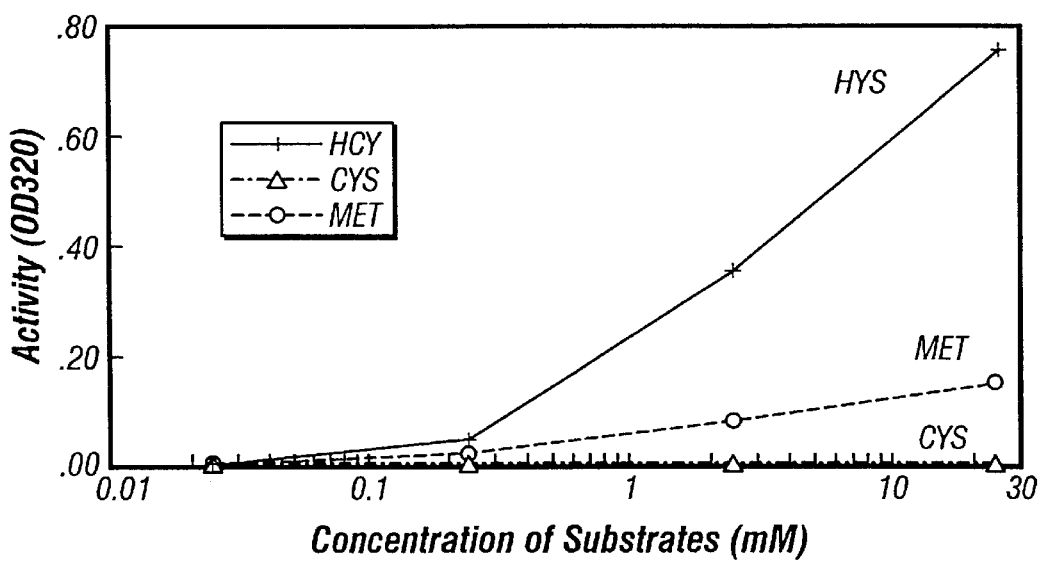
FIG. 4 shows the comparative specific activities of homocysteinase (pAC2-1 clone, purified using a nickel cation affinity reagent) for cysteine, methionine, and homocysteine.

Following use of the above initial assay screens, homocysteinases ("HCYases") from promising clones were purified using protocols that included DEAE Sepharose Fast Flow chromatography (for resultant enzyme activity profiles from the pAC2-1 clone, see FIG. 3), or included nickel-NTA affinity chromatography (for resultant enzyme activity profiles from the pAC2-1 clone, see FIG. 4).

Cell Growth Conditions

10 μl of frozen *E. coli* stock corresponding to a particular clone was seeded into 5 ml LB medium (Fisher) containing also 10 μg/ml ampicillin, and cultured overnight at 30° C. with moderate shaking (300 rpm). The culture was then divided into 2 fresh 100 ml volumes of LB medium in 500 ml flasks, and further cultured at 30° C. for 6 hours, also at 300 rpm. The entire culture was then divided into 18 flasks (each of 6 liters) containing 800 ml of LB medium. Growth was continued, overnight, at 37° C. at 300 rpm and an $OD_{600}$ of approximately 10 was achieved. The bacteria were then spun down at 4000 g permitting replacement of the growth medium with fresh LB, and the incubation was continued for a further 6 hours, again at 37° C. and 300 rpm. When the $OD_{600}$ reached 20, the bacteria were harvested by centrifugation for 10 minutes at 4000 g, 4° C. It will be recognized that a wide variety of variations on the above procedure are also effective.

Pre-Treatment Prior to Chromatography

The bacterial pellet was first suspended in extraction solution (20 mM potassium phosphate, 10 μM pyridoxal phosphate and 0.01% β-mercaptoethanol, pH 9.0), and the cells were then disrupted with a cavitator-type homogenizer (model HC 8000, Microfluidics Corporation, Newton, Mass.). The suspension was centrifuged with a refrigerated centrifuge (Sorvall, superspeed RC2-B) at 8000 g, 4° C. for 30 minutes. The supernatant was then collected, heated at 50° C. for 1 minute, and then subject to ultrafiltration using a preparative scale device (model TFF PLHK 100 k, Millipore, Bedford, Mass.) using a 2.5 ft² pressure cartridge containing 10 mM potassium phosphate buffer, pH 8.3). The pH was adjusted to 7.2 during the ultrafiltration.

Chromatographic Conditions—First Column

The above-derived concentrate (at pH 7.2) was applied to a first column (100 mm diameter×30 cm) containing a 2400 ml packed volume of DEAE Sepharose® FF (Pharmacia, Uppsala, Sweden) in 40 mM KCl-PPM buffer (40 mM potassium chloride; and 10 mM potassium phosphate, 10 μM pyridoxal phosphate, 0.01% β-mercaptoethanol, pH 7.2). After loading the protein sample, the column was pre-washed with about 10 volumes of 40 mM KCl-PPM buffer until the $OD_{280}$ dropped below 0.1. The protein was then eluted with a linear gradient of 40–300 mM KCl in PPM buffer, and 500 ml fractions were collected. The fractions containing homocysteinase were identified by their yellow color, and an activity assay.

Chromatographic Conditions—Second Column

Following a 24 hour dialysis period against a solution of 80 mM KCl, 10 mM potassium phosphate, pH 8.3, the recovered eluate (about 2–5 mg/ml representing a recovery of 5–10 total grams protein) was applied to a second column. After loading, the second column (Pharmacia XK 50/30 filled with DEAE Sepharose® FF—500 ml volume, 50 mm diameter×25 cm) was pre-washed with 4 volumes of 80 mM KCl, 10 mM potassium phosphate, pH 8.3 (at a flow rate of about 6–8 ml/minute) until the $OD_{280}$ dropped below 0.1. The homocysteinase was then eluted with a linear gradient of 80 to 300 mM potassium chloride in 10 mM potassium phosphate buffer (pH 8.3). Eluate was collected in 300 ml fractions, and active fractions were identifiable by yellow color and homocysteinase enzyme activity. Enzyme activity results (toward homocysteine, cysteine, and methionine) for homocysteinase purified in this manner are discussed in Example 8 below (see also FIG. 3).

Alternatively, an additional two stage strategy may be used. In the first stage, the partitioning material was DEAE Sepharose® FF, and loading and pre-washing were conducted with 20 mM sodium phosphate buffer, pH 7.2. Elution of the protein was accomplished using a linear gradient (8 ml/min) from 20 mM sodium phosphate buffer, pH 7.2 (solution A) to 20 mM sodium phosphate buffer, pH 7.2, 500 mM NaCl (solution B). In the second stage, the partitioning material was phenyl Sepharose® 6-FF, and loading and pre-washing were conducted with 0.6 M $NH_4SO_4$ in 20 mM sodium phosphate buffer, pH 7.2. Elution of the protein was accomplished using a linear gradient (5 ml/min) from 0.6 M $NH_4SO_4$, 20 mM sodium phosphate buffer, pH 7.2 (solution A) to 20 mM sodium phosphate buffer, pH 7.2, (solution B). The following purification results were obtained for this alternate procedure. The above-described cell-lysate contained 8400 units of homocysteinase at a specific activity (units/mg) of 5.2. Following completion of pre-column procedures, 6,300 units were recovered at a specific activity of 64 (about 75% yield). Upon completion of the DEAE Sepharose®-FF step (first column), 5,040 units were recovered at a specific activity of 172 (60% yield), while after the phenyl Sepharose® 6-FF step (second column), 4,200 units remained at a specific activity of 300 (50% yield).

Analysis of Resultant Homocysteinase

For HPLC analysis, an L-6200A Intelligent pump (Hitachi, Ltd., Tokyo, Japan) with a Supelco Progel™ TSK column (G3000 $SW_{XL}$, 30 cm×7.8 mm, Supelco, Bellefonte, Pa.) was used. Typically samples of a 20 μl size (containing about 0.1 to 0.5 mg/ml protein were loaded, and eluted with a solution of 0.12 M NaCl, 10 mM sodium phosphate buffer, pH 7.2, at a flow rate of about 1 ml/min. The protein containing fractions were identified with a spectrophotometer (Hitachi U2000) at a wavelength of 280 nm. Bovine serum albumin (MW 66,000) and β-amylase from sweet potato (MW 200,000) (Sigma, St. Louis, Mo.) were used as MW standards. Resultant retetion times were: for BSA, 8.88 min; for β-amylase, 7.82 min; and, for the product homocysteinase, 8.28 minutes.

Electrophoresis of resultant proteins was carried out on (non-reducing) 7.5% or 10% polyacrylamide-precasted plates in 0.2 M Tris-glycine buffer, pH 8.3, with and without 0.1% SDS. The molecular weight standards used were the Kaleidoscope Prestained Standards (Bio-Rad, Richmond, Calif.). The product homocysteinase resolved as a single band of about 43 kD in the presence of 0.1% SDS, and as a single band at about 172 kD absent 0.1% SDS.

DNA sequencing of suitable clones was then performed by ACGT Inc. (Northbrook, Ill.) using T7 DNA polymerase and the dideoxy nucleotide termination reaction. The primer walking method was used, and the sequences were analyzed on a DNA analyzer.

Purification of Homocysteinase as a 6x Histidine-Tagged Protein Using Ni-NTA Methodology An alternate method to purify recombinant homocysteinase from *E. coli* involves use of nickel-NTA affinity chromatography. This technology takes advantage of the affinity of protein histidine imidazoles for nickel cations immobilized in the NTA resin matrix. In order to take full advantage of this technology (Qiagen Company, Germany), a sequence of 6 additional histidine residues is added (preferably by modification of an encoding DNA which is then expressed) to the protein upstream of the N-terminus of the homocysteinase (see SEQ ID NOS 9 and 10).

According to this purification procedure (for additional information, see also "The QIAexpressionist, A handbook for high level expression and purification of 6xHis-tagged proteins" March 1997, 3rd edition, available from Qiagen) 100 ml of densely grown culture of *E. coli* BL21 (DE3), clone pAC2-1 were harvested by centrifugation, and the resultant pellet was resuspended in 4 ml lysis buffer (300 mM NaCl, 10 mM imidazole, 50 mM $NaH_2PO_4$, pH 8.0). The resultant cell suspension was then sonicated on ice for one minute.

Cellular debris was removed using a benchtop centrifuge set at maximum speed for 20 minutes. The clear supernatant was then mixed with 1 ml of Ni-NTA slurry (Qiagen), and gently shaken on ice for 60 minutes to allow adsorption. The mixture was then transferred to a disposable polypropylene column and the follow-through fraction was discarded. The Ni-NTA resin beads were then washed with 8 ml of wash buffer (300 mM NaCl, 20 mM imidazole, 50 mM $NaH_2PO_4$, pH 8.0), after which the recombinant protein was finally collected by elution using 2 ml of elution buffer (300 mM NaCl, 250 mM imidazole, 50 mM $NaH_2PO_4$, pH 8.0). The purified protein was then characterized as above. Enzyme activity results (toward homocysteine, cysteine, and methionine) for homocysteinase purified in this fashion are described in Example 2 below (see also FIG. 4).

EXAMPLE 2

Representative Catalytic Properties of the Homocysteinases of the Invention

FIGS. 2 through 4 evidence the significantly enhanced usefulness of the homocysteinases of the invention for single step assays. The results depicted in FIG. 2 reflect use of a crude lysate of the host *E. coli* cells containing the pAC2-1 clone, and show specific activity (u/mg) with respect to the 3 substrates (homocysteine, methionine, and cysteine) when each is present in a separate assay at 25 mM. The results depicted in FIGS. 3 and 4 (again for *E. coli* containing the pAC2-1 clone) reflect relative activity of purified enzyme preparations for homocysteine, methionine, and cysteine.. For the assays shown in FIG. 3, the enzyme was purified using a DEAE Sepharose Fast Flow procedure as described above for FIG. 4, a purification procedure involving nickel-NTA agarose affinity reagent, was used (see above under the heading "The α-ketobutyrate assay/pyruvate assay" for methodology).

It is well recognized that numerous procedures are available to purify recombinant homocysteinases from host *E. coli* cells. As exemplified, the novel homocysteinases of the invention exhibit activities toward homocysteine (using the assays of the invention) that are typically 100-fold, and even up to about 1000-fold, higher than their activities exhibited toward cysteine or methionine.

EXAMPLE 3

Single Step/Single Enzyme Clinical Assays

It will be immediately recognized that procedures for multi-step/multi-enzyme assays of homocysteine in biological fluids are readily adapted for use in simplified single step/single enzyme assays in order to take advantage of the substrate specificity of novel species of homocysteinase (the terms "single step assay" and "single enzyme assay" are used interchangeably herein to indicate that the biological sample need only be contacted with one enzyme in order to accurately measure homocysteine in the presence of cysteine, and/or methionine). The concentrations of homocysteinase appropriate for such procedures are readily determined.

According to the single-enzyme diagnostic methods of the invention, the concentration of homocysteine in a biological sample such as, for example, whole blood, blood plasma, serum, urine, or tissue fluid may be determined with sufficient accuracy to provide valuable diagnostic information to physicians, absent interference from contaminating concentrations of cysteine and/or methionine. Such diagnostic assays are rapid, accurate, involve a minimum of reagents, and are therefore applicable to large scale screenings operations in clinical laboratories, and as public health measures.

In a representative example, the concentration of cysteine in normal blood plasma may be about 30–120 $\mu$M ($\mu$ molar), and that of homocysteine only about 5–15 $\mu$M. As is recognized in the art, a subject's risk for cardiovascular disease may increase significantly as homocysteine concentrations in the blood plasma rise above the 15 $\mu$M level. High risk cardiovascular patients have been identified that have homocysteine levels up to several hundred $\mu$ molar. Similarly, patients affected by disorders of cysteine metabolism may have cysteine levels up to 500 or even 1000 $\mu$M. The diagnostic kits of the present invention are useful to determine homocysteine concentrations in biological fluids in the range of 1–500$\mu$ molar, for example, wherein said fluids also contain from 0$\mu$ molar (typically from 10$\mu$ molar) to about 1000$\mu$ molar of cysteine, or higher.

According to the preferred practice of the invention, homocysteinases are provided wherein the relative activities of said enzymes toward homocysteine versus cysteine are such that, by detecting product hydrogen sulfide, the apparent concentration of homocysteine measured in a patient sample (which reflects also a contribution from cysteine) is less that about 150%, preferably less than about 110%, and most preferably less than about 102%, of the actual value thereof. In a further preferred example of the invention, for example using the novel Trichomonas homocysteinase expressed from pAC2-1, the apparent concentration of homocysteine measured in a single enzyme assay reflects no more than about a 1% false contribution from cysteine.

According to the practice of the present invention, such single enzyme assay methodology (using for example, SEQ ID NO: 10 as homocysteinase) is applicable over a wide range of natural concentrations (and ratios of concentrations) of both homocysteine and cysteine (and also methionine where appropriate), and is thus accurately able to reflect the body fluid chemistry of both healthy subjects and those at risk for disease states, most particularly cardiovascular disease.

A diagnostic kit for use in the single enzyme assay of the homocysteine concentration in a biological fluid of a subject would comprise a homocysteinase enzyme; and at least one reagent capable of being used to determine the amount of product hydrogen sulfide formed by reaction of homocysteinase on homocysteine; wherein said homocysteinase is sufficiently non-reactive toward cysteine that any hydrogen sulfide produced by reaction of said bomocysteinase on cysteine does not substantially interfere with the use of said kit to assess risk for cardiovascular disease.

Since the diagnostic kits of the present invention are useful over a wide spectrum of homocysteine and cysteine concentrations, and relative concentrations, it is to be expected that there are a variety of examples of the successful practice of the invention. Representative examples are as follows:

(1) most generally, the fraction of measured hydrogen sulfide that is attributed to cysteine instead of homocysteine should be sufficiently small that it does not prevent useful interpretation of the results by a qualified medical practitioner. In general, useful diagnostic information can be obtained when the amount of produced hydrogen sulfide attributable to homocysteine is about one half of the total. Given the generally higher concentration of cysteine in patient samples, compared to homocysteine, the specificity of such enzymes is still evident. Preferably, however the fraction of total hydrogen sulfide detected in an assay that is attributable to homocysteine is at least 90%, preferably 95%, more preferably 98%, and most preferably 99% or greater. The 99% level is readily obtained according to the practice of the invention, for example using the homocysteinase represented by SEQ ID NO: 10.

(2) in an assay of a patient sample which evidences risk for cardiovascular disease, wherein the concentration of homocysteine therein is about 20μ molar or higher, concentrations of 300μ molar, or even greater, of cysteine contribute less than 1% to the total amount of hydrogen sulfide detected. Obviously such enzymes remain very useful with respect to biological samples having even greater cysteine concentrations.

(3) in an assay of a patient sample which evidences risk for cardiovascular disease, and wherein the ratio of the cysteine to homocysteine concentration is, for example, about 15:1, cysteine contributes less than about 1% to the total amount of hydrogen sulfide detected.

The following further evidences the differences between the properties of known homocysteinases and the novel enzymes of the present invention.

Homocysteinase isolated from *Trichomonas vaginalis* (which may reflect expression from more than one gene) was reported (see Lockwood et al., 1991 above) to have a $K_m$ for homocysteine of about 0.5 mM, whereas $K_m$ values determined for the novel enzyme expressed from the pAC2-1 clone are (all at 37° C., pH 8.0): 4.8 mM, 3.45 mM, and 3.1 mM for homocysteine, cysteine, and methionine, respectively.

Figure 5:
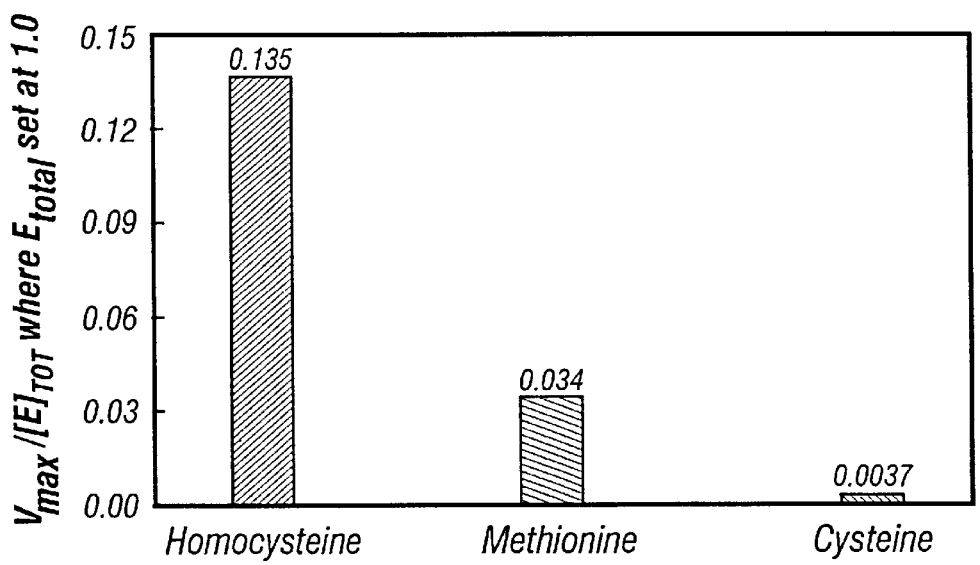
FIG. 5 shows determined $K_{cat}$ values of homocysteinase (pAC2-1 clone) for cysteine, methionine, and homocysteine.

The $K_m$ calculations were determined from assays carried out in one ml volumes of 100 mM phosphate buffer, pH 8.0 containing 10 μM pyridoxal phosphate at different concentrations (10 μM to 1.6 mM) of, separately, DL-homocysteine, L-methionine, or L-cysteine, for 10 minutes at 37° C., pH 8.0 using 50 μl of enzyme (300 units/ml). The reaction was stopped by adding 0.1 ml of 50% TCA. The resultant suspension was then centrifuged with an Eppendorf centrifuge at 13 k rpm for 2 minutes. 0.5 ml samples of supernatant were then added to 0.5 ml volumes of 0.05% 3-methyl-2-benzothiazolinone hydrazone in 0.8 ml of 1 M sodium acetate, pH 5.2, and incubated at 50° C. for 30 minutes. The amount of reaction product was then determined by spectrophotometry at $OD_{320}$. The $K_{cat}$ (turnover number) values reported in FIG. 5, were determined from the calculation of $V_{max}$ values using standard kinetic expressions and plots.

It is apparent that the kinetics of the enzyme expressed from the pAC2-1 clone are quite different from those of the prior art enzyme. An additional aspect of the present invention involves recognition that although certain changes have been described in the amino acid sequence of the *T. vaginalis* enzyme in order to provide for enhanced kinetic properties, those skilled in the art will recognize other potential mechanisms to accomplish this. An example thereof is covalent modification of the enzyme, whether or not at the active site. Such other methods of modifying a homocysteinase are within the practice of the invention if they lead to production of an enzyme having kinetic properties such as those first disclosed herein.

EXAMPLE 4

An Enhanced Detection Procedure for Hydrogen Sulfide

An enhanced methodology for the detection of hydrogen sulfide has been developed. Diagnostic kits according to this aspect of the invention are prepared as follows.

The following reagents/stock solutions are prepared:

(a) buffer solution—a stock solution of 50 mM borate buffer, pH 7.5, prepared from 309 mg $H_3BO_3$, f.w.61.83, added to 90 ml dd water, the pH is adjusted to 7.5 with NaOH, after which the volume is brought up to a total of 100 ml with dd water. Any acceptable buffer can be used in place of the borate buffer used in this example, such as sodium phosphate buffer and tris buffer.

(b) reducing agent—15.4 mg DL-dithiothreitol ("DTT"), Sigma, St. Louis, Mo., is dissolved in 1 ml of borate buffer(a) resulting in a 100 mM solution. Any acceptable reducing agent can be used in place of the DTT used in this example, such as TCEP (tris(2-carboethyl) phosphine) and β-mercapto ethanol.

(c) chromogenic reagent I—33.25 mg of potassium ferricyanate, $K_3Fe(CN)_6$, Sigma, is dissolved in a solution of 10 ml of 1N HCl, 1% (w/v) Triton X-100, Sigma, creating a 10 mM stock solution of ferric iron. This solution should be mixed well before use. Other acceptable surfactants, other than the Triton X-100 surfactant, can also be used.

(d) chromogenic reagent II—52.5 mg of N,N-dipropyl-phenylene diamine ("DPPDA"), Wako Pure Chemical Industries, Ltd., Japan, is dissolved in dd water up to a final concentration of 100 mM.

(e) recombinant homocysteinase—the enzyme represented by SEQ ID NO: 10 (derived from *E. coli* clone pAC2-1, ATCC 98549) maybe purchased as product HYase™ from AntiCancer, Inc, San Diego, Calif. and has a molecular weight of 172,000 and a specific activity of 40 units/mg. The enzyme should be diluted to 4 units/ml with borate buffer before use, stored during assays at 0–4° C., and prepared fresh for each use.

(f) DL-homocysteine—2.7 mg of DL-homocysteine, Sigma, is added to 2 ml borate buffer (4 mM final concentration), and prepared fresh daily as a calibration standard, with storage during use at 0–4° C. (Note: in general homocysteinases use only the natural L-optical isomer of homocysteine, but the D/L mixture provides an economical source of the L-isomer, requiring of course use of a correction factor of 50% to provide the effective L-concentration).

A representative assay protocol is as follows. 0.1 ml of blood plasma is added to 0.9 ml of borate buffer. 10 μl of the 100 mM DTT solution is then added, mixed well, followed by an incubation at 37° C. for 30 minutes. 30 μl of HYase™ recombinant homocysteinase (prediluted to 4 units/ml in borate buffer) is then added with mixing, followed by a further incubation period at 37° C. for 1 minute. 200 μl of chromogenic reagent I and 10 μl of chromogenic reagent II are then added simultaneously with mixing and the sample is incubated at 37° C. for 20 minutes. The product methylene blue-type chromophore is then detected by measuring the OD at 677 nm in a spectrophotometer. The plasma concentration of L-homocysteine is then determined from a constructed calibration curve, which may use homocysteine and/or the disulfide bonded dimmer thereof, homocystine, as standards. In providing this representative example, it is of course apparent that considerable variation in the selection of assay reagents or reagent concentrations is possible, and such modifications will be recognized immediately as within the skill of art.

EXAMPLE 5

A Fluorescence-Based Homocysteine Diagnostic Assay

By using fluorescence to determine the concentration of the resulting chromophore in a homocysteine assay, the sensitivity can be enhanced approximately 1000-fold in comparison to the sensitivity using absorbance. Therefore, smaller samples, about 10 to 100 fold smaller, can be analyzed using the more sensitive fluorescence-based determination than the absorbance-based determination described above. For example a blood sample derived from finger pricking is sufficient to achieve a strong fluorescence signal in the homocysteine assay.

Figure 6:
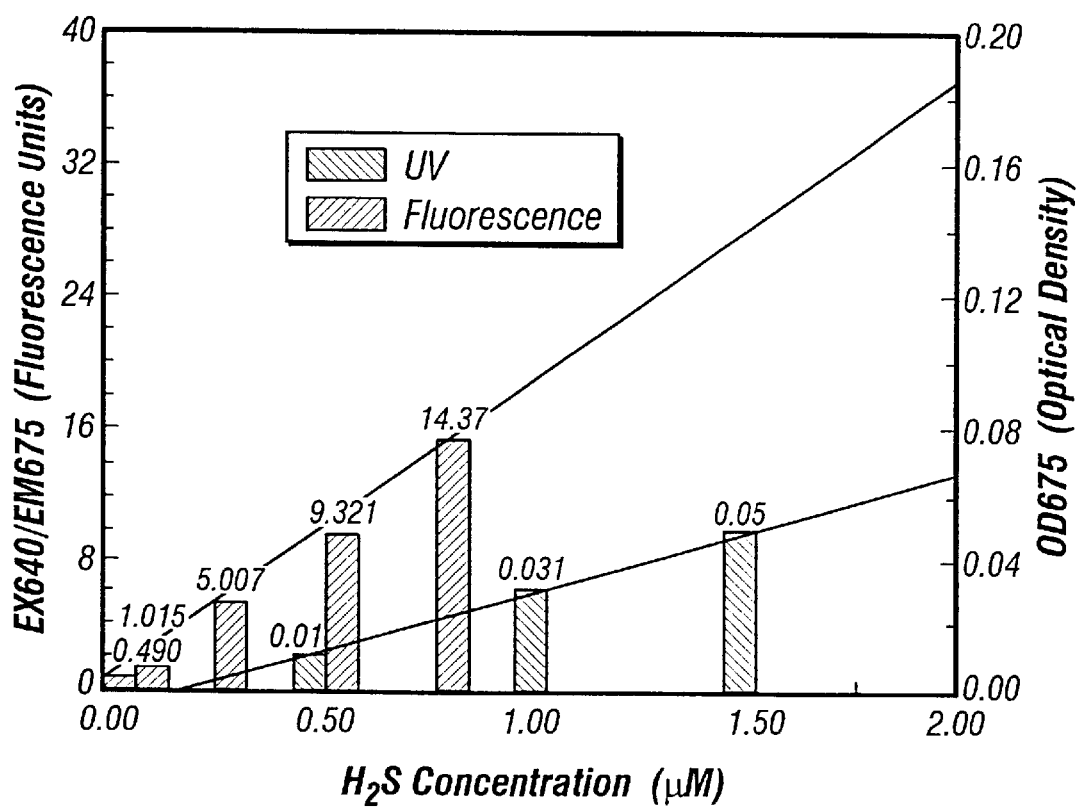
FIG. 6 provides a comparison of fluorescence and ultraviolet absorption at various hydrogen sulfide concentrations.

The increased sensitivity of the fluorescence-based assay in comparison to the absorbance-based assay is shown in FIG. 6. In this figure, the X axis represents the hydrogen sulfide concentration in the assay. The steeper curve for the fluorescence signal than for the absorbance signal for the same assay having varying concentrations demonstrates that the fluorescence signal is much more sensitive than the absorbance signal.

Any suitable reagent that provides a proper signal when measured by fluorescence is appropriate. For example, the chromogenic reagent, N,N-dibutyl-phenylene-diamine (DBPDA), used for absorbance as discussed above was used in the fluorescence-based assay illustrated in FIG. 6. Generally, the same conditions used for the absorbance-based assays can be used for the fluorescence-based assays, except the assays are measured by fluorescence.

A very strong signal by fluorescence can be obtained using an appropriate combination of excitation and emission wavelengths, which can be determined by one having ordinary skill in the art. For example, excitation at 665 nm and emission at 690 nm, or excitation at 640 nm and emission at 675 can be used under certain conditions.

Figure 7:
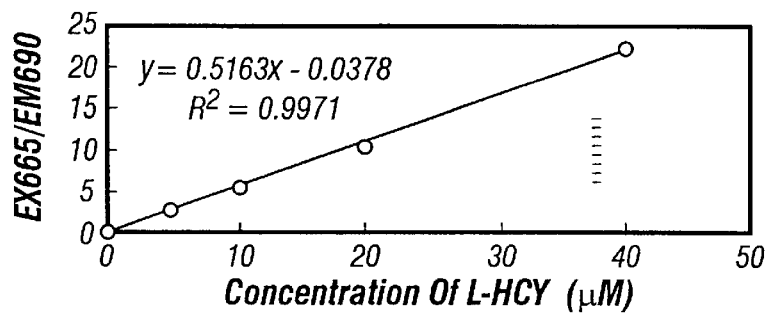
FIG. 7 shows the standard curve of L-homocysteine.
Figure 8:
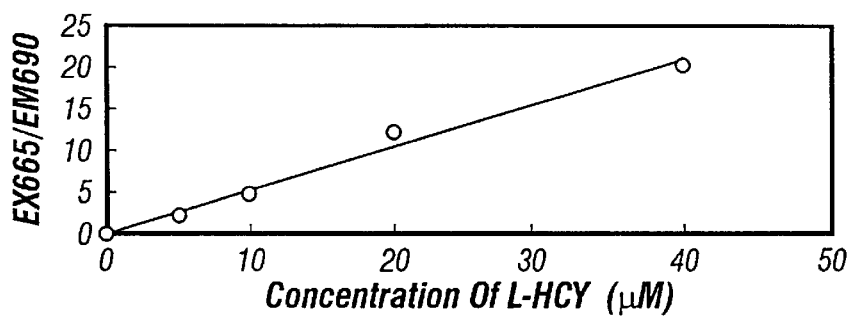
FIG. 8 shows a curve of homocysteine demonstrating the relative lack of interference by cysteine in an enzymatic homocysteine assay measured by fluorescence and results of a blood sample derived from finger pricking.
Figure 9:
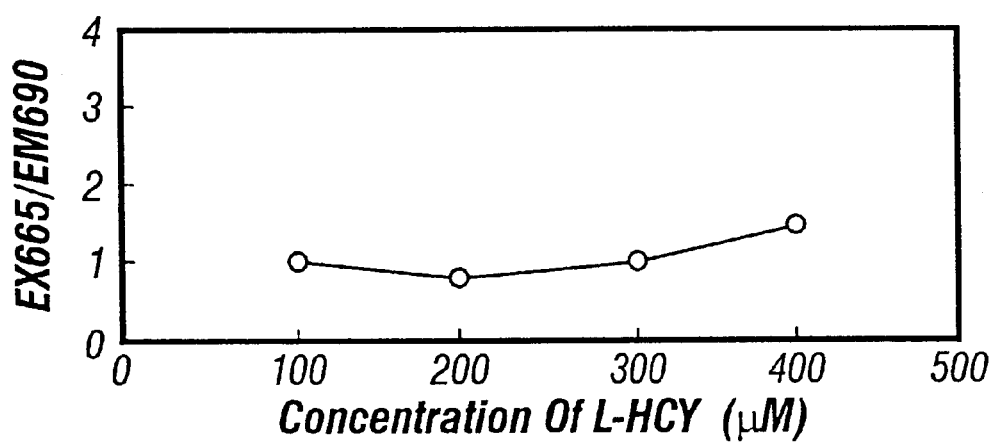
FIG. 9 shows the interference of cysteine measured by fluorescence at various concentrations of cysteine.

A comparison of FIG. 7 standard curve for homocysteine, based on measurements by fluorescence, and FIG. 8 curve for homocysteine samples that also contain a fixed amount of cysteine, shows that cysteine has minimal interference with the homocysteine measurement. These results are consistent with absorbance-based assays. FIG. 9 shows the interference by cysteine samples of varying concentrations.

A small sample of blood derived from finger pricking was used to determine the homocysteine concentration therein. Corresponding the fluorescence readout of the sample with the appropriate concentration in the standard curve in FIG. 7 gave the concentration shown in the results in the chart in FIG. 7.

EXAMPLE 6

Additional Methodology

The following provides additional examples of procedures, and variations thereof, which the practitioner may find useful in the practice of the invention.

Growth of Recombinant Bacteria

Each fermentation run was started with one vial of recombinant *E. coli* containing recombinant homocysteinase (pAC2-1, see SEQ ID NOS: 9 and 10) from the master cell bank (MCB). Ten microliters of bacteria from the MCB were seeded into 5 ml LB medium and grown overnight at 37° C. with shaking at 400 rpm. The culture was transferred to 800 ml LB medium in 6 L flasks and grown overnight at 37° C. at 400 rpm at which time the $OD_{600}$ was approximately 10. The bacteria were collected by centrifugation at 4000 rpm for 20 min. The bacteria were then transferred into 800-ml LB-medium cultures in 6 L flasks and grown at 37° C. at 400 rpm for 16 h. The bacteria were harvested by centrifugation at 4000 rpm at 4° C. for 20 minutes.

Precolumn Treatment

The bacterial pellets, derived from 90x 800-ml cultures of recombinant *E. coli,* were combined and disrupted with a cavitation type homogenizer (Microfluidics Corp., Newton, Mass.; model HC 8000). The homogenate was suspended in 2 vol. of 20 mM potassium phosphate pH 7.2 containing 10 μM pyridoxal phosphate, 0.01% β-mercaptoethanol and 20% ethanol. Heat treatment of the homogenate was carried out at 50° C. for 1 minute. 1% (w/v) polyethylenimine (PEI) was added to the suspension solution and mixed for 20 minutes. The suspension was centrifuged with an automatic refrigerated centrifuge (Sorvall, Superspeed RC 2-B) at 4° C. at 12,000 rpm for 40 minutes to remove nucleic acids. The supernatant was then collected and mixed with polyethylene glycol 8000 (PEG 8000) to a final concentration of 10–12% (w/v) and stirred at 4° C. for 60 minutes. The precipitate (containing contaminating proteins) was removed by centrifugation at 12,000 rpm for 40 minutes. 3.0 M sodium chloride was then added to the supernatant to give a final concentration of 0.12 M which precipitated recombinant homocysteinase. The pellet was collected by centrifugation at 12,000 rpm for 40 minutes and dissolved in 20 mM potassium phosphate buffer pH 7.6, containing 10 μM pyridoxal phosphate and 0.01% β-mercaptoethanol.

DEAE-Sepharose FF Chromatograph

The enzyme sample from the precolumn treatment was applied to a column of DEAE-Sepharose FF (30×5 cm) (Pharmacia) that was previously equilibrated with 20 mM potassium phosphate pH 7.2. After loading the column, it was prewashed with 50 mM sodium chloride, 20 mM potassium phosphate pH 7.2 for approximately 3 volumes, until the $OD_{280}$ dropped below 0.1. Recombinant homocysteinase was then eluted with a linear sodium chloride concentration gradient of 0.05–0.5 M in the same buffer over 90 minutes.

Phenyl-Sepharose 6 FF Chromatography

Solid ammonium sulfate (79.3 mg/ml) was added to the active fractions of the DEAE-Sepharose FF chromatography to give a final concentration of 0.6 M. Before loading the supernatant on the Phenyl-Sepharose 6 FF column (20×2.6 cm), the column was equilibrated with Buffer A—consisting of 0.6 M ammonium sulfate in 20 mM potassium phosphate pH 7.6. Bound protein was eluted by linearly decreasing the ammonium sulfate gradient with Buffer B (which contained 20 mM potassium phosphate pH 7.6, 10 μM pyridoxal phosphate, 0.02% β-mercaptoethanol, and 5.0% ethylene glycol). The active fractions were concentrated by DEAE-Sepharose FF (20×1.6 cm) which removed ammonium sulfate and polyethylene glycol. Purified enzyme was stored at −80° C.

Activity Assays for Recombinant Homocysteinase

An activity assay for the keto product of the α, γ or α,β-elimination (α-keto butyrate for homocysteine) was carried out in a 1.5 ml Eppindorf tube using 1-ml. of 50 mM phosphate buffer pH 8.0 (also containing 10 μM pyridoxal phosphate and 20 mM homocysteine) for 10 minutes at 37° C., with varying amounts of enzyme. The reaction was stopped by adding 0.5 ml of 4.5% TCA. 0.05 ml of the resultant solution was then combined with 0.45 ml of 0.05% 3-methyl-2-benzothiazothiazolinone hydrazone (MBTH) and added to a 1.0 ml sample of 1.0 M sodium acetate, pH 5.2, followed by incubation at 50° C. for 30 minutes.

The amount of reaction product was determined by spectrophotometry at $OD_{335}$. The hydrazone product has an extinction coefficient of $7.6 \times 10^3$ l/mol×cm.. The amount of protein was determined with the Lowry Reagent Kit (Sigma) with bovine serum albumin as a standard. The specific activity was calculated as units/mg protein, with one unit of enzyme defined as the amount that catalyzed the formation of 1 μmol of α-ketobutyrate/minute.

Activity assays for the γ and β elimination reactions of homocysteine and cysteine, respectively, were carried out at 37° C. for 30 seconds. The resulting $H_2S$ produced was measured using methylene blue formation at $OD_{671}$.

SDS-PAGE and PAGE

Electrophoresis was performed according to the methods described in the NOVEX Kit (NOVEX Experimental Technology, San Diego). A 12% Tris-Gel was used for SDS-PAGE. After staining with Coomassie brilliant blue, the intensity of protein bands was estimated with molecular standards (NOVEX mark 12 Wide Range Protein Standard), including myosin, 200 kD; β-galactosidase, 116.3 kD; phosphorylase b, 97.4 kD; bovine serum albumin, 66.3 kD; carbonic anhydrase, 31.0 kD; trypsin inhibitor, 21.5 kD; lysozyme, 14.4 kD; aprotinin, 6.0 kD. Native gels were stained for recombinant homocysteinase activity by immersion in a reaction mixture containing 3.3 mM-DL-homocysteine, 0.33 mM lead acetate, 28.4 mM β-mercaptoethanol, and 100 mM Tris-HCl buffer, pH 7.5. Bands containing homocysteinase activity will convert homocysteine to α-ketobutyrate, ammonia and $H_2S$. Hydrogen sulfide reacts with lead acetate to form a dark brown precipitate ($Pb_2S$). The gels were then stained for protein with Coomassie Blue.

In further support of the present disclosure, on Sep. 26, 1997, a deposit of biological material of confirmed viability was made with the American Type Culture Collection, Rockville, Md., USA under the Budapest Treaty. The material is identified as *E. coli* BL21 (DE3), clone pAC2-1, and has been assigned ATCC number 98549. Upon the granting of a patent herein, all restrictions on the availability of this material to the public will be irrevocably removed.

What is claimed is:

1. A purified and isolated homocycsteinase which has the amino acid sequence of SEQ. ID No. 10 or variant thereof wherein said homocysteinase has the property that at least about 90% of the hydrogen sulfide produced by action of said homocysteinase upon contacting a biological fluid is contributed by homocysteine, when the concentrations of homocysteine and cysteine in said fluid are, respectively, about 5–15$\mu$ molar and about 100–300$\mu$ molar respectively.

2. The homocysteinase of claim 1 wherein at least about 99% of the hydrogen sulfide produced by action of said homocysteinase upon contacting a biological fluid is contributed by homocysteine when the concentrations of homocysteine and cysteine in said fluid are, respectively, about 5–15$\mu$ molar and about 100–300$\mu$ molar.

3. The homocysteinase of claim 1 wherein at least about 90% of the hydrogen sulfide produced by action of said homocysteinase upon contacting a biological fluid is contributed by homocysteine when the fluid contains 5$\mu$ molar homocysteine 1000$\mu$ molar cysteine.

4. The homocysteinase of claim 1 which has the amino acid sequence of a desulfurase derived from Pseudomonas, Clostridium, Aeromonas or Trichomonas or a mutated form thereof.

5. The homocysteinase of claim 1 which further comprises at least one histidine residue at the N-terminus.

6. A purified and isolated homocysteinase which has the amino acid sequence of SEQ. ID No. 10 or variant thereof having desulfurase activity to homocysteine as a substrate compared to cysteine as a substrate such that the amount of hydrogen sulfide liberated from treatment of a sample of blood, urine, tissue fluid, serum, or plasma of a subject with said enzyme is substantially generated from the homocysteine and not from the cysteine in said sample, when the concentration of homocysteine is ten fold less than the concentration of cysteine in said sample.

7. The homocysteinase of claim 6 which has the amino acid sequence of a desulfurase derived from Pseudomonas Clostridium, Aeromonas or Trichomonas or a mutated form thereof.

8. The homocysteinase of claim 6 which further comprises at least one histidine residue at the N-terminus.

9. A purified and isolated homocysteinase which has the amino acid sequence of SEQ. ID No. 10 or variant thereof having desulfurase activity to homocysteine as a substrate at least 100 times greater than that to cysteine as a substrate when said substrates are present in a physiological fluid.

10. The homocysteinase of claim 9 which has the amino acid sequence of a desulfurase derived from Pseudomonas, Clostridium, Aeromonas or Trichomonas, or a mutated form thereof.

11. The homocysteinase of claim 9 which further comprises at least one histidine residue at the N-terminus.

12. A purified and isolated homocysteinase which has at least about 110% of the activity of the homocysteinase of SEQ ID No. 10 toward homocysteine and no more than about 90% of the activity of the homocysteinase of SEQ ID No. 10 toward cysteine or methionine in a suitable assay.

13. The homocysteinase of claim 12 which has the amino acid sequence of a desulfurase derived from Pseudomonas, Clostridium, Aeromonas or Trichomonas, or a mutated form thereof.

14. The homocysteinase of claim 12 which further comprises at least one histidine residue at the N-terminus.

15. A purified and isolated nucleotide sequence which encodes the homocysteinase of any of claims 1, 6, 9, or 12.

16. A DNA or RNA molecule which comprises an expression system which expression system consists essentially of the nucleotide sequence of claim 15 operably linked to control sequences for its expression.

17. A recombinant host cell modified to contain the DNA or RNA molecule of claim 16.

18. A method to prepare a homocysteinase having a high specificity for homocysteine as compared to cysteine which method comprises culturing the cells of claim 17 under conditions wherein said homocysteinase is produced.

* * * * *

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 12 amino acids
      (B) TYPE: amino acid
      (C) STRANDEDNESS: single
      (D) TOPOLOGY: linear (xi) SEQUENCE DESCRIPTION: SEQ ID NO:1:

```
Cys Ser Arg Ala Asp Ile Ile Ala Lys Val Lys Ser
1               5                   10
```

(2) INFORMATION FOR SEQ ID NO:2:

(i) SEQUENCE CHARACTERISTICS:
      (A) LENGTH: 12 amino acids
      (B) TYPE: amino acid
      (C) STRANDEDNESS: single
      (D) TOPOLOGY: linear (xi) SEQUENCE DESCRIPTION: SEQ ID NO:2:

```
Val Gly Ser Gln Ala Leu Val Asp Arg Ile Arg Leu
1               5                   10
```

(2) INFORMATION FOR SEQ ID NO:3:

(i) SEQUENCE CHARACTERISTICS:
      (A) LENGTH: 3 amino acids
      (B) TYPE: amino acid
      (C) STRANDEDNESS: single
      (D) TOPOLOGY: linear (xi) SEQUENCE DESCRIPTION: SEQ ID NO:3:

```
Asp Val Asp
1
```

(2) INFORMATION FOR SEQ ID NO:4:

(i) SEQUENCE CHARACTERISTICS:
      (A) LENGTH: 3 amino acids
      (B) TYPE: amino acid
      (C) STRANDEDNESS: single
      (D) TOPOLOGY: linear (xi) SEQUENCE DESCRIPTION: SEQ ID NO:4:

Glu Leu Lys
1

(2) INFORMATION FOR SEQ ID NO:5:

(i) SEQUENCE CHARACTERISTICS:
      (A) LENGTH: 4 amino acids
      (B) TYPE: amino acid
      (C) STRANDEDNESS: single
      (D) TOPOLOGY: linear (xi) SEQUENCE DESCRIPTION: SEQ ID NO:5:

Cys His Val Val
1

(2) INFORMATION FOR SEQ ID NO:6:

(i) SEQUENCE CHARACTERISTICS:
      (A) LENGTH: 4 amino acids
      (B) TYPE: amino acid
      (C) STRANDEDNESS: single
      (D) TOPOLOGY: linear (xi) SEQUENCE DESCRIPTION: SEQ ID NO:6:

Ala Leu Gln Leu
1

(2) INFORMATION FOR SEQ ID NO:7:

(i) SEQUENCE CHARACTERISTICS:
      (A) LENGTH: 10 amino acids
      (B) TYPE: amino acid
      (C) STRANDEDNESS: single
      (D) TOPOLOGY: linear (xi) SEQUENCE DESCRIPTION: SEQ ID NO:7:

Cys Glu Asn Val Gln Asp Ile Ile Asp Asp
1            5                10

(2) INFORMATION FOR SEQ ID NO:8:

(i) SEQUENCE CHARACTERISTICS:
      (A) LENGTH: 10 amino acids
      (B) TYPE: amino acid
      (C) STRANDEDNESS: single
      (D) TOPOLOGY: linear (xi) SEQUENCE DESCRIPTION: SEQ ID NO:8:

Gly Leu Glu Asp Ile Asp Asp Leu Leu Ala
1            5                10

(2) INFORMATION FOR SEQ ID NO:9:

(i) SEQUENCE CHARACTERISTICS:
      (A) LENGTH: 1240 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 18..1226

(ix) FEATURE:
      (A) NAME/KEY: mat_peptide
      (B) LOCATION: 39

(xi) SEQUENCE DESCRIPTION: SEQ ID NO:9:

```
AAGAAGGAGA TATACAT ATG CAT CAT CAT CAT CAT CAC ATG TCT CAC GAG          50
                Met His His His His His His Met Ser His Glu
                 -7      -5                       1

AGA ATG ACC CCA GCA ACA GCA TGC ATC CAT GCT AAT CCA CAG AAG GAT          98
Arg Met Thr Pro Ala Thr Ala Cys Ile His Ala Asn Pro Gln Lys Asp
 5           10                  15                      20

CAG TTT GGA GCA GCC ATC CCA CCA ATC TAC CAA ACA TCA ACA TTC GTT         146
Gln Phe Gly Ala Ala Ile Pro Pro Ile Tyr Gln Thr Ser Thr Phe Val
                 25                  30                  35

TTC GAT AAC TGC CAA CAG GGT GGA AAC AGA CTC GCT GGT CAG GAA TCC         194
Phe Asp Asn Cys Gln Gln Gly Gly Asn Arg Leu Ala Gly Gln Glu Ser
                 40                  45                  50

GGC TAC ATC TAC ACA CGT CTC GGC AAC CCA ACA GTT TCA AAC CTC GAA         242
Gly Tyr Ile Tyr Thr Arg Leu Gly Asn Pro Thr Val Ser Asn Leu Glu
             55                  60                  65

GGC AAG ATC GCC TTC CTC GAG AAA ACA GAA GCA TGC GTT GCC ACA TCT         290
Gly Lys Ile Ala Phe Leu Glu Lys Thr Glu Ala Cys Val Ala Thr Ser
             70                  75                  80

TCT GGC ATG GGT GCC ATT GCT GCT ACA GTT TTG ACA ATC CTC AAG GCC         338
Ser Gly Met Gly Ala Ile Ala Ala Thr Val Leu Thr Ile Leu Lys Ala
 85              90                  95                     100

GGA GAT CAC TTA ATC TCC GAT GAG TGC CTT TAT GGC TGC ACA CAT GCT         386
Gly Asp His Leu Ile Ser Asp Glu Cys Leu Tyr Gly Cys Thr His Ala
                105                 110                 115

CTC TTT GAG CAC GCA TTG ACA AAG TTC GGC ATC CAG GTC GAC TTC ATC         434
Leu Phe Glu His Ala Leu Thr Lys Phe Gly Ile Gln Val Asp Phe Ile
                120                 125                 130

AAC ACA GCC ATC CCA GGC GAG GTC AAG AAG CAC ATG AAG CCA AAC ACA         482
Asn Thr Ala Ile Pro Gly Glu Val Lys Lys His Met Lys Pro Asn Thr
            135                 140                 145

AAG ATT GTC TAT TTC GAG ACA CCA GCC AAC CCA ACA CTC AAG ATC ATC         530
Lys Ile Val Tyr Phe Glu Thr Pro Ala Asn Pro Thr Leu Lys Ile Ile
            150                 155                 160

GAC ATG GAG CGC GTC TGC AAG GAA GCC CAC AGC CAG GAG GGC GTC TTA         578
Asp Met Glu Arg Val Cys Lys Glu Ala His Ser Gln Glu Gly Val Leu
165             170                 175                 180

GTT ATC GCC GAT AAC ACA TTC TGC TCA CCA ATG ATC ACA AAC CCA GTC         626
Val Ile Ala Asp Asn Thr Phe Cys Ser Pro Met Ile Thr Asn Pro Val
                185                 190                 195

GAC TTT GGC GTC GAT GTT GTT GTC CAC TCT GCA ACA AAG TAC ATC AAC         674
Asp Phe Gly Val Asp Val Val Val His Ser Ala Thr Lys Tyr Ile Asn
                200                 205                 210

GGC CAC ACA GAT GTC GTC GCT GGC CTT ATC TGT GGC AAG GCT GAC CTC         722
Gly His Thr Asp Val Val Ala Gly Leu Ile Cys Gly Lys Ala Asp Leu
            215                 220                 225

CTT CAA CAG ATT CGT ATG GTT GGT ATC AAG GAT ATC ACA GGA TCT GTT         770
Leu Gln Gln Ile Arg Met Val Gly Ile Lys Asp Ile Thr Gly Ser Val
            230                 235                 240

ATC AGC CCA CAC GAC GCT TGG CTC ATC ACA CGT GGC CTC TCA ACA CTC         818
Ile Ser Pro His Asp Ala Trp Leu Ile Thr Arg Gly Leu Ser Thr Leu
245             250                 255                 260

AAC ATC AGA ATG AAG GCT GAG AGC GAG AAC GCC ATG AAG GTC GCT GAG         866
Asn Ile Arg Met Lys Ala Glu Ser Glu Asn Ala Met Lys Val Ala Glu
                265                 270                 275

TAC CTC AAA TCT CAC CCA GCC GTT GAG AAG GTT TAC TAC CCA GGC TTC         914
Tyr Leu Lys Ser His Pro Ala Val Glu Lys Val Tyr Tyr Pro Gly Phe
                280                 285                 290

GAG GAC CAC GAG GGC CAC GAT ATC GCT AAG AAG CAG ATG AGA ATG TAC         962
Glu Asp His Glu Gly His Asp Ile Ala Lys Lys Gln Met Arg Met Tyr
```

```
                295                 300                 305
GGT TCA ATG ATC ACA TTC ATC CTC AAG TCC GGC TTC GAA GGC GCT AAG    1010
Gly Ser Met Ile Thr Phe Ile Leu Lys Ser Gly Phe Glu Gly Ala Lys
    310                 315                 320

AAG CTC CTC GAC AAC CTC AAG CTT ATC ACA CTT GCA GTT TCC CTT GGT    1058
Lys Leu Leu Asp Asn Leu Lys Leu Ile Thr Leu Ala Val Ser Leu Gly
325                 330                 335                 340

GGC TGC GAG TCC CTC ATC CAG CAC CCA GCT TCA ATG ACT CAC GCT GTC    1106
Gly Cys Glu Ser Leu Ile Gln His Pro Ala Ser Met Thr His Ala Val
            345                 350                 355

GTT CCA AAG GAG GAG CGT GAG GCC GCT GGT ATT ACA GAT GGC ATG ATC    1154
Val Pro Lys Glu Glu Arg Glu Ala Ala Gly Ile Thr Asp Gly Met Ile
                360                 365                 370

CGC CTT TCT GTC GGT ATT GAA GAT GCC GAC GAA CTC ATC GCT GAT TTC    1202
Arg Leu Ser Val Gly Ile Glu Asp Ala Asp Glu Leu Ile Ala Asp Phe
        375                 380                 385

AAA CAG GGC CTT GAC GCT CTT TTA TAAGGATCCT CTAG                    1240
Lys Gln Gly Leu Asp Ala Leu Leu
    390                 395
```

(2) INFORMATION FOR SEQ ID NO:10:

(i) SEQUENCE CHARACTERISTICS:
        (A) LENGTH: 403 amino acids
        (B) TYPE: amino acid
        (D) TOPOLOGY: linear (ii) MOLECULE TYPE: protein (xi) SEQUENCE DESCRIPTION: SEQ ID NO:10:

```
Met His His His His His His Met Ser His Glu Arg Met Thr Pro Ala
-7      -5                  1               5

Thr Ala Cys Ile His Ala Asn Pro Gln Lys Asp Gln Phe Gly Ala Ala
10              15                  20                  25

Ile Pro Pro Ile Tyr Gln Thr Ser Thr Phe Val Phe Asp Asn Cys Gln
                30                  35                  40

Gln Gly Gly Asn Arg Leu Ala Gly Gln Glu Ser Gly Tyr Ile Tyr Thr
            45                  50                  55

Arg Leu Gly Asn Pro Thr Val Ser Asn Leu Glu Gly Lys Ile Ala Phe
        60                  65                  70

Leu Glu Lys Thr Glu Ala Cys Val Ala Thr Ser Ser Gly Met Gly Ala
    75                  80                  85

Ile Ala Ala Thr Val Leu Thr Ile Leu Lys Ala Gly Asp His Leu Ile
90                  95                  100                 105

Ser Asp Glu Cys Leu Tyr Gly Cys Thr His Ala Leu Phe Glu His Ala
            110                 115                 120

Leu Thr Lys Phe Gly Ile Gln Val Asp Phe Ile Asn Thr Ala Ile Pro
        125                 130                 135

Gly Glu Val Lys Lys His Met Lys Pro Asn Thr Lys Ile Val Tyr Phe
    140                 145                 150

Glu Thr Pro Ala Asn Pro Thr Leu Lys Ile Ile Asp Met Glu Arg Val
    155                 160                 165

Cys Lys Glu Ala His Ser Gln Glu Gly Val Leu Val Ile Ala Asp Asn
170                 175                 180                 185

Thr Phe Cys Ser Pro Met Ile Thr Asn Pro Val Asp Phe Gly Val Asp
            190                 195                 200

Val Val Val His Ser Ala Thr Lys Tyr Ile Asn Gly His Thr Asp Val
            205                 210                 215
```

```
Val Ala Gly Leu Ile Cys Gly Lys Ala Asp Leu Leu Gln Gln Ile Arg
    220                 225                 230

Met Val Gly Ile Lys Asp Ile Thr Gly Ser Val Ile Ser Pro His Asp
    235                 240                 245

Ala Trp Leu Ile Thr Arg Gly Leu Ser Thr Leu Asn Ile Arg Met Lys
250                 255                 260                 265

Ala Glu Ser Glu Asn Ala Met Lys Val Ala Glu Tyr Leu Lys Ser His
                270                 275                 280

Pro Ala Val Glu Lys Val Tyr Tyr Pro Gly Phe Glu Asp His Glu Gly
            285                 290                 295

His Asp Ile Ala Lys Lys Gln Met Arg Met Tyr Gly Ser Met Ile Thr
        300                 305                 310

Phe Ile Leu Lys Ser Gly Phe Glu Gly Ala Lys Lys Leu Leu Asp Asn
    315                 320                 325

Leu Lys Leu Ile Thr Leu Ala Val Ser Leu Gly Gly Cys Glu Ser Leu
330                 335                 340                 345

Ile Gln His Pro Ala Ser Met Thr His Ala Val Pro Lys Glu Glu
                350                 355                 360

Arg Glu Ala Ala Gly Ile Thr Asp Gly Met Ile Arg Leu Ser Val Gly
            365                 370                 375

Ile Glu Asp Ala Asp Glu Leu Ile Ala Asp Phe Lys Gln Gly Leu Asp
380                 385                 390

Ala Leu Leu
    395
```

(2) INFORMATION FOR SEQ ID NO:11:

(i) SEQUENCE CHARACTERISTICS:
        (A) LENGTH: 1191 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1188
        (D) OTHER INFORMATION: /codon_start= 1

(ix) FEATURE:
        (A) NAME/KEY: mat_peptide
        (B) LOCATION: 1

(xi) SEQUENCE DESCRIPTION: SEQ ID NO:11:

```
ATG TCT CAC GAG AGA ATG ACC CCA GCA ACA GCA TGC ATC CAT GCT AAT        48
Met Ser His Glu Arg Met Thr Pro Ala Thr Ala Cys Ile His Ala Asn
 1               5                  10                  15

CCA CAG AAG GAT CAG TTT GGA GCA GCC ATC CCA CCA ATC TAC CAA ACA        96
Pro Gln Lys Asp Gln Phe Gly Ala Ala Ile Pro Pro Ile Tyr Gln Thr
                20                  25                  30

TCA ACA TTC GTT TTC GAT AAC TGC CAA CAG GGT GGA AAC AGA TTC GCT       144
Ser Thr Phe Val Phe Asp Asn Cys Gln Gln Gly Gly Asn Arg Phe Ala
            35                  40                  45

GGT CAG GAA TCC GGC TAC ATC TAC ACA CGT CTC GGC AAC CCA ACA GTT       192
Gly Gln Glu Ser Gly Tyr Ile Tyr Thr Arg Leu Gly Asn Pro Thr Val
        50                  55                  60

TCA AAC CTC GAA GGC AAG ATC GCC TTC CTC GAG AAA ACA GAA GCA TGC       240
Ser Asn Leu Glu Gly Lys Ile Ala Phe Leu Glu Lys Thr Glu Ala Cys
65                  70                  75                  80

GTT GCC ACA TCT TCT GGC ATG GGT GCC ATT GCT GCT ACA GTT TTG ACA       288
Val Ala Thr Ser Ser Gly Met Gly Ala Ile Ala Ala Thr Val Leu Thr
```

-continued

|  |  |  |  |  |  |  |  |  |  |  |  |  |  |  |  |
|---|---|---|---|---|---|---|---|---|---|---|---|---|---|---|---|
|  |  |  |  | 85 |  |  |  |  | 90 |  |  |  |  | 95 |  |
| ATC | CTC | AAG | GCC | GGA | GAT | CAC | TTA | ATC | TCC | GAT | GAG | TGC | CTT | TAT | GGC | 336
| Ile | Leu | Lys | Ala | Gly | Asp | His | Leu | Ile | Ser | Asp | Glu | Cys | Leu | Tyr | Gly |
|  |  |  | 100 |  |  |  | 105 |  |  |  | 110 |  |  |  |  |
| TGC | ACA | CAT | GCT | CTC | TTT | GAG | CAC | GCA | TTG | ACA | AAG | TTC | GGC | ATC | CAG | 384
| Cys | Thr | His | Ala | Leu | Phe | Glu | His | Ala | Leu | Thr | Lys | Phe | Gly | Ile | Gln |
|  |  | 115 |  |  |  | 120 |  |  |  | 125 |  |  |  |  |  |
| GTC | GAC | TTC | ATC | AAC | ACA | GCC | ATC | CCA | GGC | GAG | GTC | AAG | AAG | CAC | ATG | 432
| Val | Asp | Phe | Ile | Asn | Thr | Ala | Ile | Pro | Gly | Glu | Val | Lys | Lys | His | Met |
|  | 130 |  |  |  | 135 |  |  |  | 140 |  |  |  |  |  |  |
| AAG | CCA | AAC | ACA | AAG | ATT | GTC | TAT | TTC | GAG | ACA | CCA | GCC | AAC | CCA | ACA | 480
| Lys | Pro | Asn | Thr | Lys | Ile | Val | Tyr | Phe | Glu | Thr | Pro | Ala | Asn | Pro | Thr |
| 145 |  |  |  | 150 |  |  |  | 155 |  |  |  | 160 |  |  |  |
| CTC | AAG | ATC | ATC | GAC | ATG | GAG | CGC | GTC | TGC | AAG | GAC | GCC | CAC | AGC | CAG | 528
| Leu | Lys | Ile | Ile | Asp | Met | Glu | Arg | Val | Cys | Lys | Asp | Ala | His | Ser | Gln |
|  |  |  | 165 |  |  |  | 170 |  |  |  | 175 |  |  |  |
| GAG | GGC | GTC | TTA | GTT | ATC | GCC | GAT | AAC | ACA | TTC | TGC | TCA | CCA | ATG | ATC | 576
| Glu | Gly | Val | Leu | Val | Ile | Ala | Asp | Asn | Thr | Phe | Cys | Ser | Pro | Met | Ile |
|  |  |  | 180 |  |  |  | 185 |  |  |  | 190 |  |  |  |  |
| ACA | AAC | CCA | GTC | GAC | TTT | GGC | GTC | GAT | GTT | GTT | GTC | CAC | TCT | GCA | ACA | 624
| Thr | Asn | Pro | Val | Asp | Phe | Gly | Val | Asp | Val | Val | Val | His | Ser | Ala | Thr |
|  |  | 195 |  |  |  | 200 |  |  |  | 205 |  |  |  |  |  |
| AAG | TAC | ATC | AAC | GGC | CAC | ACA | GAT | GTC | GTC | GCT | GGC | CTT | ATC | TGT | GGC | 672
| Lys | Tyr | Ile | Asn | Gly | His | Thr | Asp | Val | Val | Ala | Gly | Leu | Ile | Cys | Gly |
| 210 |  |  |  | 215 |  |  |  | 220 |  |  |  |  |  |  |  |
| AAG | GCT | GAC | CTC | CTT | CAA | CAG | ATT | CGT | ATG | GTT | GGT | ATC | AAG | GAT | ATC | 720
| Lys | Ala | Asp | Leu | Leu | Gln | Gln | Ile | Arg | Met | Val | Gly | Ile | Lys | Asp | Ile |
| 225 |  |  |  | 230 |  |  |  | 235 |  |  |  | 240 |  |  |  |
| ACA | GGA | TCT | GTT | ATC | AGC | CCA | CAC | GAC | GCT | TGG | CTC | ATC | ACA | CGT | GGC | 768
| Thr | Gly | Ser | Val | Ile | Ser | Pro | His | Asp | Ala | Trp | Leu | Ile | Thr | Arg | Gly |
|  |  |  | 245 |  |  |  | 250 |  |  |  | 255 |  |  |  |  |
| CTC | TCA | ACA | CTC | AAC | ATC | AGA | ATG | AAG | GCT | GAG | AGC | GAG | AAC | GCC | ATG | 816
| Leu | Ser | Thr | Leu | Asn | Ile | Arg | Met | Lys | Ala | Glu | Ser | Glu | Asn | Ala | Met |
|  |  | 260 |  |  |  | 265 |  |  |  | 270 |  |  |  |  |  |
| AAG | GTC | GCT | GAG | TAC | CTC | AAA | TCT | CAC | CCA | GCC | GTT | GAG | AAG | GTT | TAC | 864
| Lys | Val | Ala | Glu | Tyr | Leu | Lys | Ser | His | Pro | Ala | Val | Glu | Lys | Val | Tyr |
|  | 275 |  |  |  | 280 |  |  |  | 285 |  |  |  |  |  |  |
| TAC | CCA | GGC | TTC | GAG | GAC | CAC | GAG | GGC | CAC | GAT | ATC | GCT | AAG | AAG | CAG | 912
| Tyr | Pro | Gly | Phe | Glu | Asp | His | Glu | Gly | His | Asp | Ile | Ala | Lys | Lys | Gln |
| 290 |  |  |  | 295 |  |  |  | 300 |  |  |  |  |  |  |  |
| ATG | AGA | ATG | TCG | GGT | TCA | ATG | ATC | ACA | TTC | ATC | CTC | AAG | TCC | GGC | TTC | 960
| Met | Arg | Met | Ser | Gly | Ser | Met | Ile | Thr | Phe | Ile | Leu | Lys | Ser | Gly | Phe |
| 305 |  |  |  | 310 |  |  |  | 315 |  |  |  | 320 |  |  |  |
| GAA | GGC | GCT | AAG | AAG | CTC | CTC | GAC | AAC | CTC | AAG | CTT | ATC | ACA | CTT | GCA | 1008
| Glu | Gly | Ala | Lys | Lys | Leu | Leu | Asp | Asn | Leu | Lys | Leu | Ile | Thr | Leu | Ala |
|  |  |  | 325 |  |  |  | 330 |  |  |  | 335 |  |  |  |  |
| GTT | TCC | CTT | GGT | GGC | TGC | GAG | TCC | CTC | ATC | CAG | CAC | CCA | GCT | TCA | ATG | 1056
| Val | Ser | Leu | Gly | Gly | Cys | Glu | Ser | Leu | Ile | Gln | His | Pro | Ala | Ser | Met |
|  |  | 340 |  |  |  | 345 |  |  |  | 350 |  |  |  |  |  |
| ACT | CAC | GCT | GTC | GTT | CCA | AAG | GAG | GAG | CGT | GAG | GCC | GCT | GGT | ATT | ACA | 1104
| Thr | His | Ala | Val | Val | Pro | Lys | Glu | Glu | Arg | Glu | Ala | Ala | Gly | Ile | Thr |
|  | 355 |  |  |  | 360 |  |  |  | 365 |  |  |  |  |  |  |
| GAT | GGC | ATG | ATC | CGC | CTT | TCT | GTC | GGT | ATT | GAA | GAT | GCC | GAC | GAA | CTC | 1152
| Asp | Gly | Met | Ile | Arg | Leu | Ser | Val | Gly | Ile | Glu | Asp | Ala | Asp | Glu | Leu |
|  | 370 |  |  |  | 375 |  |  |  | 380 |  |  |  |  |  |  |
| ATC | GCT | GAT | TTC | AAA | CAG | GGC | CTT | GAC | GCT | CTT | TTA | TAA |  |  |  | 1191
| Ile | Ala | Asp | Phe | Lys | Gln | Gly | Leu | Asp | Ala | Leu | Leu |  |  |  |  |
| 385 |  |  |  | 390 |  |  |  | 395 |  |  |  |  |  |  |  |

(2) INFORMATION FOR SEQ ID NO:12:

(i) SEQUENCE CHARACTERISTICS:
        (A) LENGTH: 396 amino acids
        (B) TYPE: amino acid
        (D) TOPOLOGY: linear (ii) MOLECULE TYPE: protein (xi) SEQUENCE DESCRIPTION: SEQ ID NO:12:

```
Met Ser His Glu Arg Met Thr Pro Ala Thr Ala Cys Ile His Ala Asn
 1               5                  10                  15

Pro Gln Lys Asp Gln Phe Gly Ala Ala Ile Pro Ile Tyr Gln Thr
                20                  25                  30

Ser Thr Phe Val Phe Asp Asn Cys Gln Gln Gly Gly Asn Arg Phe Ala
                35                  40                  45

Gly Gln Glu Ser Gly Tyr Ile Tyr Thr Arg Leu Gly Asn Pro Thr Val
        50                  55                  60

Ser Asn Leu Glu Gly Lys Ile Ala Phe Leu Glu Lys Thr Glu Ala Cys
65                  70                  75                  80

Val Ala Thr Ser Ser Gly Met Gly Ala Ile Ala Ala Thr Val Leu Thr
                85                  90                  95

Ile Leu Lys Ala Gly Asp His Leu Ile Ser Asp Glu Cys Leu Tyr Gly
                100                 105                 110

Cys Thr His Ala Leu Phe Glu His Ala Leu Thr Lys Phe Gly Ile Gln
            115                 120                 125

Val Asp Phe Ile Asn Thr Ala Ile Pro Gly Glu Val Lys Lys His Met
        130                 135                 140

Lys Pro Asn Thr Lys Ile Val Tyr Phe Glu Thr Pro Ala Asn Pro Thr
145                 150                 155                 160

Leu Lys Ile Ile Asp Met Glu Arg Val Cys Lys Asp Ala His Ser Gln
                165                 170                 175

Glu Gly Val Leu Val Ile Ala Asp Asn Thr Phe Cys Ser Pro Met Ile
            180                 185                 190

Thr Asn Pro Val Asp Phe Gly Val Asp Val Val His Ser Ala Thr
        195                 200                 205

Lys Tyr Ile Asn Gly His Thr Asp Val Val Ala Gly Leu Ile Cys Gly
    210                 215                 220

Lys Ala Asp Leu Leu Gln Gln Ile Arg Met Val Gly Ile Lys Asp Ile
225                 230                 235                 240

Thr Gly Ser Val Ile Ser Pro His Asp Ala Trp Leu Ile Thr Arg Gly
                245                 250                 255

Leu Ser Thr Leu Asn Ile Arg Met Lys Ala Glu Ser Glu Asn Ala Met
            260                 265                 270

Lys Val Ala Glu Tyr Leu Lys Ser His Pro Ala Val Glu Lys Val Tyr
        275                 280                 285

Tyr Pro Gly Phe Glu Asp His Glu Gly His Asp Ile Ala Lys Lys Gln
    290                 295                 300

Met Arg Met Ser Gly Ser Met Ile Thr Phe Ile Leu Lys Ser Gly Phe
305                 310                 315                 320

Glu Gly Ala Lys Lys Leu Leu Asp Asn Leu Lys Leu Ile Thr Leu Ala
                325                 330                 335

Val Ser Leu Gly Gly Cys Glu Ser Leu Ile Gln His Pro Ala Ser Met
            340                 345                 350

Thr His Ala Val Val Pro Lys Glu Glu Arg Glu Ala Ala Gly Ile Thr
        355                 360                 365
```

```
Asp Gly Met Ile Arg Leu Ser Val Gly Ile Glu Asp Ala Asp Glu Leu
    370                 375                 380

Ile Ala Asp Phe Lys Gln Gly Leu Asp Ala Leu Leu
385                 390                 395
```

(2) INFORMATION FOR SEQ ID NO:13:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:13:

GGATTACATA TGCATCATCA TCATCATCAC ATGAGTGGCC ACGCTATCGA C          51

(2) INFORMATION FOR SEQ ID NO:14:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:14:

GGATTAGGAT CCTTAGAGGA CTAAGTCGAG AGCC          34

(2) INFORMATION FOR SEQ ID NO:15:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:15:

ATCGCTAGCA TATGATCCCG GACGTATCAC AG          32

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:16:

ATCACCATCC ACTGGTGTAA TG          22

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:17:

CTACCGATTT TGCGGAAG          18

(2) INFORMATION FOR SEQ ID NO:18:

(i) SEQUENCE CHARACTERISTICS:
        (A) LENGTH: 30 base pairs
        (B) TYPE: nucleic acid
        (C) STRANDEDNESS: single -continued

```
        (D) TOPOLOGY: linear (xi) SEQUENCE DESCRIPTION: SEQ ID NO:18:

CATGACGGAT CCTCAGGCGT GTTTTTCCAG                                    30

(2) INFORMATION FOR SEQ ID NO:19:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:19:

ATCGCTAGCA TATGCATCAT CATCATCATC ACATGATCCC GGACGTATC               49
```